(12) United States Patent
Goossens et al.

(10) Patent No.: US 7,622,634 B2
(45) Date of Patent: Nov. 24, 2009

(54) USE OF GENES ENCODING MEMBRANE TRANSPORTER PUMPS TO STIMULATE THE PRODUCTION OF SECONDARY METABOLITES IN BIOLOGICAL CELLS

(75) Inventors: Alain Goossens, Lokeren (BE); Dirk Gustaaf Inze, Moorsel-Aalst (BE); Kirsi-Marja Oksman-Caldentey, Helsinki (FI); Into J. Laakso, Espoo (FI)

(73) Assignee: VTT Biotechnology (FI)

( * ) Notice: Subject to any disclaimer, the term of this patent is extended or adjusted under 35 U.S.C. 154(b) by 1099 days.

(21) Appl. No.: 10/666,778

(22) Filed: Sep. 18, 2003

(65) Prior Publication Data

US 2004/0064849 A1 Apr. 1, 2004

Related U.S. Application Data

(63) Continuation of application No. PCT/EP02/04322, filed on Apr. 18, 2002.

(30) Foreign Application Priority Data

Apr. 18, 2001 (EP) .................................. 01201407

(51) Int. Cl.
- C12N 15/09 (2006.01)
- C12N 15/12 (2006.01)
- C12N 15/29 (2006.01)
- C12N 15/31 (2006.01)
- A01H 5/00 (2006.01)

(52) U.S. Cl. ........................ 800/288; 800/296; 800/298; 435/419; 536/23.1; 536/23.5; 536/23.6; 536/23.74

(58) Field of Classification Search ................. 800/288, 800/298; 435/419, 320.1; 536/23.1, 23.6, 536/23.7, 23.74

See application file for complete search history.

(56) References Cited

U.S. PATENT DOCUMENTS

| | | | |
|---|---|---|---|
| 5,239,044 A | 8/1993 | Cooper et al. | |
| 5,552,307 A | 9/1996 | Kessler et al. | |
| 5,599,977 A | 2/1997 | Kiely et al. | |
| 5,831,043 A | 11/1998 | Fleche | |
| 6,049,004 A | 4/2000 | Kiely et al. | |
| 6,054,637 A | 4/2000 | Boller et al. | |
| 6,069,009 A | 5/2000 | Pepin et al. | |
| 6,166,290 A | 12/2000 | Rea et al. | |

FOREIGN PATENT DOCUMENTS

| | | | |
|---|---|---|---|
| WO | WO 98/21938 | * | 5/1998 |
| WO | WO 99/10514 | | 3/1999 |
| WO | WO 00/18886 | | 4/2000 |
| WO | WO 00/46383 | | 8/2000 |
| WO | WO 01/07621 A2 | | 2/2001 |
| WO | WO 02/083888 | | 10/2002 |

OTHER PUBLICATIONS

Theodoulou F. Biochemica et Biophysica Acta; 2000, 1465, pp. 79-103.*
Dudler R. et al. Journal of Biological Chemistry; Mar. 25, 1992, vol. 267, No. 9 pp. 5582-5888.*
Sidler M. et al. The Plant Cell, Oct. 1998; vol. 10, 1623-1635.*
Jasinski M. et al. Bulletin de la Societe Royale des Sciences de Leige; 1999, vol. 68, No. 5-6 p. 323.*
Jasinski M. et al. The Plant Cell, May 2001; vol. 13, pp. 1095-1107.*
Muhitch, M. et al. Plant Science, 2000, vol. 157, pp. 201-207.*
Hamill, J., et al. Plant Molecular Biology, vol. 15, 1990 pp. 27-38.*
Hallard D. et al. Plant Cell Reports, 1997, vol. 17; pp. 50-54.*
Balzi et al., PDR5, a Novell Yeast Multidrug Resistance Conferring Transporter Controlled by the Transcription Regulator PDR1, The Journal of Biological Chemistry, Jan. 21, 1994, pp. 2206-2214, vol. 269, No. 3.
Del Sorbo et al., Review, Fungal Transporters Involved in Efflux of Natural Toxic Compounds and Fungicides, Fungal Genetics and Biology, 2000, pp. 1-15, vol. 30.
Klein et al., The ABC-like vacuolar transporter for rye mesophyll flavone glucuronides is not species-specific, Phytochemistry, 2001, pp. 153-159, vol. 56.
Kolaczkowski et al., Anticancer Drugs, Ionophoric Peptides, and Steroids as Substrates of the Yeast Multidrug Transporter Pdr5p, The Journal of Biological Chemistry, Dec. 6, 1996, pp. 31543-31548, vol. 271, No. 49.
Kolaczkowski et al., In Vivo Characterization of the Drug Resistance Profile of the Major ABC Transporters and Other Components of the Yeast Pleiotropic Drug Resistance Network, Microbial Drug Resistance, 1998, pp. 143-158, vol. 4, No. 3.
Theodoulou et al., Review, Plant ABC transporters, Biochimica et Biophysica Acta, 2000, pp. 79-103, vol. 1465.

* cited by examiner

Primary Examiner—Russell Kallis
(74) Attorney, Agent, or Firm—TraskBritt

(57) ABSTRACT

The invention relates to the field of secondary metabolite production in plants and plant cell cultures. More specifically, the invention relates to the use of transporters and more particularly ABC-transporters to enhance the production and/or secretion of secondary metabolites in plants and plant cell cultures.

23 Claims, 3 Drawing Sheets

```
                            SEQUENCE LISTING

<160> NUMBER OF SEQ ID NOS: 15

<210> SEQ ID NO 1
<211> LENGTH: 4571
<212> TYPE: DNA
<213> ORGANISM: Hyoscyamus muticus
<220> FEATURE:
<221> NAME/KEY: CDS
<222> LOCATION: (133)..(4407)
<223> OTHER INFORMATION: n is defined as any nucleotide

<400> SEQUENCE: 1
atataactaa  cttcaccttc  tattcattca  ttatcaacaa  aataatccat  tttttatcaa        60
aacttgaagg  tgttgttaca  agacacaact  aatattaatt  gctgcatttt  aatttaatct       120
tgttgttcca  ac atg gag cca tca gat tta agt aat ttc cga ggt cga agt         171
              Met Glu Pro Ser Asp Leu Ser Asn Phe Arg Gly Arg Ser
                1               5                  10 atg aga gga agt atg aga gga agt gta agg gaa aat agt aac tca ata              219
Met Arg Gly Ser Met Arg Gly Ser Val Arg Glu Asn Ser Asn Ser Ile
     15                  20                  25 tgg agg aac aat gga gtt gaa ata ttt tca aga tca act aga gat gaa              267
Trp Arg Asn Asn Gly Val Glu Ile Phe Ser Arg Ser Thr Arg Asp Glu
 30                  35                  40                  45 gat gat gaa gag gca tta aaa tgg gca gca ctt gag aaa tta cca aca              315
Asp Asp Glu Glu Ala Leu Lys Trp Ala Ala Leu Glu Lys Leu Pro Thr
                 50                  55                  60 tat gat aga tta aga aaa ggt ata ttg ttt gga tca caa ggt act ggt              363
Tyr Asp Arg Leu Arg Lys Gly Ile Leu Phe Gly Ser Gln Gly Thr Gly
             65                  70                  75 gtt gct gaa gtt gat gta gat gat ctt ggt gtt caa caa agg aag aat              411
Val Ala Glu Val Asp Val Asp Asp Leu Gly Val Gln Gln Arg Lys Asn
         80                  85                  90 ttg ctt gac aga ctt gtt aaa att gct gaa gaa gat aat gag aag ttc              459
Leu Leu Asp Arg Leu Val Lys Ile Ala Glu Glu Asp Asn Glu Lys Phe
     95                 100                 105 ttg ttg aaa ctc aag aac agg att gac agg gtt ggg att gat ttt cca              507
Leu Leu Lys Leu Lys Asn Arg Ile Asp Arg Val Gly Ile Asp Phe Pro
110                 115                 120                 125 tct ata gaa gtg aga ttt gag cat ctg aat att gag gca gat gca tat              555
Ser Ile Glu Val Arg Phe Glu His Leu Asn Ile Glu Ala Asp Ala Tyr
                130                 135                 140 gtt ggt agc aga gct ttg cct aca ttt acc aac ttc att tct aac ttc              603
Val Gly Ser Arg Ala Leu Pro Thr Phe Thr Asn Phe Ile Ser Asn Phe
            145                 150                 155 att gag tcc ctg ctg gat tca ctt cac atc ctt cca tcg aaa aaa cgt              651
Ile Glu Ser Leu Leu Asp Ser Leu His Ile Leu Pro Ser Lys Lys Arg
        160                 165                 170 tca gtt aca att ctc aag gat gtt agt ggt atc gtc aag ccc tgt cga              699
Ser Val Thr Ile Leu Lys Asp Val Ser Gly Ile Val Lys Pro Cys Arg
    175                 180                 185 atg act ctg ctt tta gga cct cca ggt tct ggg aaa aca act ttg tta              747
```

```
                                                            -continued

Met Thr Leu Leu Leu Gly Pro Pro Gly Ser Gly Lys Thr Thr Leu Leu
190             195                 200                 205 ctt gct ttg gct gga aaa ctt gat tct gct cta agg gtt acg ggg aag      795
Leu Ala Leu Ala Gly Lys Leu Asp Ser Ala Leu Arg Val Thr Gly Lys
                210                 215                 220 gtg acg tat aat gga cac gaa tta cat gaa ttt gtg cca caa aga act      843
Val Thr Tyr Asn Gly His Glu Leu His Glu Phe Val Pro Gln Arg Thr
            225                 230                 235 gcg gcc tat att agc cag cat gat ttg cat att gga gaa atg act gtc      891
Ala Ala Tyr Ile Ser Gln His Asp Leu His Ile Gly Glu Met Thr Val
        240                 245                 250 aga gaa act ttg gag ttc tct gca aga tgc caa gga gtt ggt tct cgt      939
Arg Glu Thr Leu Glu Phe Ser Ala Arg Cys Gln Gly Val Gly Ser Arg
    255                 260                 265 tac gaa atg ttg gcc gaa ctg tca aga aga gag aaa gcg gct aat atc      987
Tyr Glu Met Leu Ala Glu Leu Ser Arg Arg Glu Lys Ala Ala Asn Ile
270                 275                 280                 285 aaa cca gat gct gat att gac atg ttc atg aag gct gca tca act gaa     1035
Lys Pro Asp Ala Asp Ile Asp Met Phe Met Lys Ala Ala Ser Thr Glu
                290                 295                 300 ggg caa gaa gcc aaa gtg att act gat tat gtt ctt aag att ctg gga     1083
Gly Gln Glu Ala Lys Val Ile Thr Asp Tyr Val Leu Lys Ile Leu Gly
            305                 310                 315 ctg gat att tgt gca gat act atg gtg gga gat caa atg ata agg ggt     1131
Leu Asp Ile Cys Ala Asp Thr Met Val Gly Asp Gln Met Ile Arg Gly
        320                 325                 330 att tca gga gga cag aag aag cgt gtc act act ggt gaa atg att gtc     1179
Ile Ser Gly Gly Gln Lys Lys Arg Val Thr Thr Gly Glu Met Ile Val
    335                 340                 345 gga ccg tct aaa gcc ctt ttc atg gat gaa att tca act gga ctt gac     1227
Gly Pro Ser Lys Ala Leu Phe Met Asp Glu Ile Ser Thr Gly Leu Asp
350                 355                 360                 365 agt tcc aca act tac tcc atc gtg aat tcc cta aag caa tct gtt caa     1275
Ser Ser Thr Thr Tyr Ser Ile Val Asn Ser Leu Lys Gln Ser Val Gln
                370                 375                 380 atc ttg aaa gga aca gct ctg att tct ctc ttg cag cct gcc ccc gag     1323
Ile Leu Lys Gly Thr Ala Leu Ile Ser Leu Leu Gln Pro Ala Pro Glu
            385                 390                 395 act tac aac ttg ttc gat gat att gtt ctg cta tca gat ggc tac att     1371
Thr Tyr Asn Leu Phe Asp Asp Ile Val Leu Leu Ser Asp Gly Tyr Ile
        400                 405                 410 gtt tat cag ggt cca cga gag gaa gtg ctc gat ttc ttt gaa tcc atg     1419
Val Tyr Gln Gly Pro Arg Glu Glu Val Leu Asp Phe Phe Glu Ser Met
    415                 420                 425 gga ttc aaa tgc ccc aac aga aaa ggc gtg gct gac ttc ttg caa gaa     1467
Gly Phe Lys Cys Pro Asn Arg Lys Gly Val Ala Asp Phe Leu Gln Glu
430                 435                 440                 445 gtt aca tct aag aag gat caa cag caa tat tgg gta aag agg gac gag     1515
Val Thr Ser Lys Lys Asp Gln Gln Gln Tyr Trp Val Lys Arg Asp Glu
                450                 455                 460 cct tat agg ttt att aca tca aaa gaa ttt gct gag gct tat caa tct     1563
Pro Tyr Arg Phe Ile Thr Ser Lys Glu Phe Ala Glu Ala Tyr Gln Ser
            465                 470                 475 ttc cat gtt ggg aga aaa gta agc gat gaa ctt aca acc gca ttt gac     1611
Phe His Val Gly Arg Lys Val Ser Asp Glu Leu Thr Thr Ala Phe Asp
        480                 485                 490 aag agc aaa agc cac cct gct gct ttg act act gaa aag tat ggt att     1659
Lys Ser Lys Ser His Pro Ala Ala Leu Thr Thr Glu Lys Tyr Gly Ile
    495                 500                 505
```

```
gga gtg aaa caa ctt ttg aag gtt tgc acg gaa aga gag ttc ctt cta    1707
Gly Val Lys Gln Leu Leu Lys Val Cys Thr Glu Arg Glu Phe Leu Leu
510             515                 520                 525 atg cag agg aat tca ttt gtt tac atc ttc aaa ttc ttt cag ctt atg    1755
Met Gln Arg Asn Ser Phe Val Tyr Ile Phe Lys Phe Phe Gln Leu Met
                530                 535                 540 gta att gca ctt atg aca atg acc ata ttt ttt cga act aag atg tct    1803
Val Ile Ala Leu Met Thr Met Thr Ile Phe Phe Arg Thr Lys Met Ser
            545                 550                 555 cgg gat act gag acc gat gga gga att tat tct ggt gct ctc ttt ttt    1851
Arg Asp Thr Glu Thr Asp Gly Gly Ile Tyr Ser Gly Ala Leu Phe Phe
        560                 565                 570 acg gtt gtt atg ctt atg ttt aat ggt ttg tct gag ctt cct ttg aca    1899
Thr Val Val Met Leu Met Phe Asn Gly Leu Ser Glu Leu Pro Leu Thr
    575                 580                 585 ctc tac aag ctc ccg gtc ttc tac aag caa agg gac ttt ctc ttc tat    1947
Leu Tyr Lys Leu Pro Val Phe Tyr Lys Gln Arg Asp Phe Leu Phe Tyr
590                 595                 600                 605 cct tca tgg gct tat gca gtt cct tca tgg atc cta aaa atc cct gta    1995
Pro Ser Trp Ala Tyr Ala Val Pro Ser Trp Ile Leu Lys Ile Pro Val
                610                 615                 620 act ttt ctt gaa gtt ggg atg tgg gtg ttt ctc acc tat tat gtc atc    2043
Thr Phe Leu Glu Val Gly Met Trp Val Phe Leu Thr Tyr Tyr Val Ile
            625                 630                 635 gga ttt gat cct aat gtt gga aga ttt ttc aaa caa ttt ttg cta ctc    2091
Gly Phe Asp Pro Asn Val Gly Arg Phe Phe Lys Gln Phe Leu Leu Leu
        640                 645                 650 ata gta gta aac cag atg gca tca gga ttg ttc agg ttt att gca gca    2139
Ile Val Val Asn Gln Met Ala Ser Gly Leu Phe Arg Phe Ile Ala Ala
    655                 660                 665 gtt gga agg acc atg gga gtt gct agc aca ttt gga gca ttt gcg ctg    2187
Val Gly Arg Thr Met Gly Val Ala Ser Thr Phe Gly Ala Phe Ala Leu
670                 675                 680                 685 ctt tta caa ttt gca ttg ggc ggt ttt gtc ctt gca cga act gac gtg    2235
Leu Leu Gln Phe Ala Leu Gly Gly Phe Val Leu Ala Arg Thr Asp Val
                690                 695                 700 aag gac tgg tgg att tgg gga tac tgg acc tca cca ctt atg ttc tca    2283
Lys Asp Trp Trp Ile Trp Gly Tyr Trp Thr Ser Pro Leu Met Phe Ser
            705                 710                 715 gtg aat gca atc ctt gtg aat gaa ttt gac gga aaa aag tgg aaa cat    2331
Val Asn Ala Ile Leu Val Asn Glu Phe Asp Gly Lys Lys Trp Lys His
        720                 725                 730 att gcg cca aat gga act gag ccg ctt gga cct gca gtg gta aga tct    2379
Ile Ala Pro Asn Gly Thr Glu Pro Leu Gly Pro Ala Val Val Arg Ser
    735                 740                 745 caa ggg ttc ttt ccc gat gca tat tgg tac tgg ata ggt gta ggt gca    2427
Gln Gly Phe Phe Pro Asp Ala Tyr Trp Tyr Trp Ile Gly Val Gly Ala
750                 755                 760                 765 ctt gtt gga ttc aca gtt ctg ttt aac ata gcc tac agt ctt gct ctc    2475
Leu Val Gly Phe Thr Val Leu Phe Asn Ile Ala Tyr Ser Leu Ala Leu
                770                 775                 780 gct tat ctt aac cca ttc gga aag cca caa gct aca att tca gaa gaa    2523
Ala Tyr Leu Asn Pro Phe Gly Lys Pro Gln Ala Thr Ile Ser Glu Glu
            785                 790                 795 agt gag agc aac gaa aat agt gaa tta tca acc cca ata gct agt aca    2571
Ser Glu Ser Asn Glu Asn Ser Glu Leu Ser Thr Pro Ile Ala Ser Thr
        800                 805                 810 acg gaa gga gat tct gtc ggt gag aat cag aat aag aaa gga atg gtt    2619
Thr Glu Gly Asp Ser Val Gly Glu Asn Gln Asn Lys Lys Gly Met Val
    815                 820                 825
```

```
ctt cca ttt gaa ccc cat tcc atc acc ttt gat gaa gtt gta tac tca    2667
Leu Pro Phe Glu Pro His Ser Ile Thr Phe Asp Glu Val Val Tyr Ser
830                 835                 840                 845 gtt gac atg cct ccg gaa atg aga gag caa ggt acc agt gac aat aga    2715
Val Asp Met Pro Pro Glu Met Arg Glu Gln Gly Thr Ser Asp Asn Arg
                850                 855                 860 ttg gta ctt ttg aag agt gtg agt gga gct ttc agg cca ggt gtt ctc    2763
Leu Val Leu Leu Lys Ser Val Ser Gly Ala Phe Arg Pro Gly Val Leu
        865                 870                 875 aca gct ctg atg gga gtt agt gga gcc ggt aaa aca aca ttg atg gat    2811
Thr Ala Leu Met Gly Val Ser Gly Ala Gly Lys Thr Thr Leu Met Asp
            880                 885                 890 gtc tta gct gga agg aaa act gga ggt tac att gac gga agc att aac    2859
Val Leu Ala Gly Arg Lys Thr Gly Gly Tyr Ile Asp Gly Ser Ile Asn
895                 900                 905 att tct gga tat ccc aag aag caa gaa aca ttt gca cgt att tct gga    2907
Ile Ser Gly Tyr Pro Lys Lys Gln Glu Thr Phe Ala Arg Ile Ser Gly
910                 915                 920                 925 tac tgt gaa caa aac gac atc cat tca cct tat gta aca gtt tat gag    2955
Tyr Cys Glu Gln Asn Asp Ile His Ser Pro Tyr Val Thr Val Tyr Glu
                930                 935                 940 tcc ttg gtt tac tcg gct tgg ctg cgt tta cct caa gac gtt gat gag    3003
Ser Leu Val Tyr Ser Ala Trp Leu Arg Leu Pro Gln Asp Val Asp Glu
        945                 950                 955 aaa aag cga atg atg ttc gtt gaa caa gtt atg gaa ctt gtg gag ctt    3051
Lys Lys Arg Met Met Phe Val Glu Gln Val Met Glu Leu Val Glu Leu
            960                 965                 970 aca cca cta aga tct gcc tta gtc ggg ttg cca gga gtt aat ggt ctg    3099
Thr Pro Leu Arg Ser Ala Leu Val Gly Leu Pro Gly Val Asn Gly Leu
975                 980                 985 acg att gca gtt gaa cta gta gca aac ccc tct  atc att ttt atg gac   3147
Thr Ile Ala Val Glu Leu Val Ala Asn Pro Ser  Ile Ile Phe Met Asp
990                 995                 1000                1005 gaa cca act tca gga  ttg gat gca aga gct  gct gca att gtg atg      3192
Glu Pro Thr Ser Gly  Leu Asp Ala Arg Ala  Ala Ala Ile Val Met
                1010                1015                1020 aga gct gtt agg aac  act gtc gat aca ggg  aga act gtt gtt tgt      3237
Arg Ala Val Arg Asn  Thr Val Asp Thr Gly  Arg Thr Val Val Cys
                1025                1030                1035 acc att cat cag cct  agc att gac att ttt  gag gcg ttc gat gag      3282
Thr Ile His Gln Pro  Ser Ile Asp Ile Phe  Glu Ala Phe Asp Glu
                1040                1045                1050 tta ttt ctt atg aaa  cga gga gga caa gag  ata tac gtc ggt cca      3327
Leu Phe Leu Met Lys  Arg Gly Gly Gln Glu  Ile Tyr Val Gly Pro
                1055                1060                1065 tta ggt cgt gag tca  agc cat ttg ata aag  tat ttt gag tct ata      3372
Leu Gly Arg Glu Ser  Ser His Leu Ile Lys  Tyr Phe Glu Ser Ile
                1070                1075                1080 ccc ggt gta acc aaa  ata aag gag ggg tac  aat cca gca act tgg      3417
Pro Gly Val Thr Lys  Ile Lys Glu Gly Tyr  Asn Pro Ala Thr Trp
                1085                1090                1095 atg tta gaa gtc aca  tct tcg tct caa gaa  ata aca tta ggt gtt      3462
Met Leu Glu Val Thr  Ser Ser Ser Gln Glu  Ile Thr Leu Gly Val
                1100                1105                1110 gat ttt acc gaa tta  tac aag aac tca gac  ctc ttc cgg agg aac      3507
Asp Phe Thr Glu Leu  Tyr Lys Asn Ser Asp  Leu Phe Arg Arg Asn
                1115                1120                1125 aaa gct ttg atc gag  gaa cta agt gtg cca  cgc cct ggt aca agt      3552
Lys Ala Leu Ile Glu  Glu Leu Ser Val Pro  Arg Pro Gly Thr Ser
```

-continued

```
                   1130                1135                1140
gac ctg cat ttt gaa  act gaa ttc tca cag  cca ttt tgg gtc caa           3597
Asp Leu His Phe Glu  Thr Glu Phe Ser Gln  Pro Phe Trp Val Gln
         1145                1150                1155 tgt atg gct tgt ttg  tgg aag caa cac tgg  tca tac tgg cgt aat           3642
Cys Met Ala Cys Leu  Trp Lys Gln His Trp  Ser Tyr Trp Arg Asn
         1160                1165                1170 ccg gct tat act gca  gtc aga ttt ctc ttc  aca acc ttc ata gct           3687
Pro Ala Tyr Thr Ala  Val Arg Phe Leu Phe  Thr Thr Phe Ile Ala
         1175                1180                1185 ctc ata ttc ggg tca  atg ttc tgg gat att  ggt aca aaa gtg agt           3732
Leu Ile Phe Gly Ser  Met Phe Trp Asp Ile  Gly Thr Lys Val Ser
         1190                1195                1200 ggg ccc caa gat ctg  aaa aac gcc atg gga  tct atg tat gct gct           3777
Gly Pro Gln Asp Leu  Lys Asn Ala Met Gly  Ser Met Tyr Ala Ala
         1205                1210                1215 gtc ctc ttc ctt ggt  gtg cag aat tca tcg  tca gtt cag ccc gtt           3822
Val Leu Phe Leu Gly  Val Gln Asn Ser Ser  Ser Val Gln Pro Val
         1220                1225                1230 gta tct gtc gaa cgt  act gta ttt tac aga  gaa aaa gct gct gga           3867
Val Ser Val Glu Arg  Thr Val Phe Tyr Arg  Glu Lys Ala Ala Gly
         1235                1240                1245 atg tac tcc gcg atg  ccc tat gcc ttt gca  caa gtt ttc atc gaa           3912
Met Tyr Ser Ala Met  Pro Tyr Ala Phe Ala  Gln Val Phe Ile Glu
         1250                1255                1260 att cct tat gta ttt  gta caa gct gtt gtc  tat ggt ctc att gtc           3957
Ile Pro Tyr Val Phe  Val Gln Ala Val Val  Tyr Gly Leu Ile Val
         1265                1270                1275 tat tct atg att gga  ttt gaa tgg act gct  gca aaa ttc ttt tgg           4002
Tyr Ser Met Ile Gly  Phe Glu Trp Thr Ala  Ala Lys Phe Phe Trp
         1280                1285                1290 tac ttc ttc ttc atg  ttc ttc acc ttc ctc  tac ttc acc ttc ttt           4047
Tyr Phe Phe Phe Met  Phe Phe Thr Phe Leu  Tyr Phe Thr Phe Phe
         1295                1300                1305 ggc atg atg acc gtg  gct gtt acc ccg aac  caa aat gtt gct tca           4092
Gly Met Met Thr Val  Ala Val Thr Pro Asn  Gln Asn Val Ala Ser
         1310                1315                1320 atc gtt gcc gga ttc  ttc tat aca gta tgg  aat ctc ttc tca gga           4137
Ile Val Ala Gly Phe  Phe Tyr Thr Val Trp  Asn Leu Phe Ser Gly
         1325                1330                1335 ttc atc gtt cca cga  cct cgt att ccg ata  tgg tgg aga tgg tac           4182
Phe Ile Val Pro Arg  Pro Arg Ile Pro Ile  Trp Trp Arg Trp Tyr
         1340                1345                1350 tac tgg gct tgc cct  gtt gca tgg aca ttg  tat ggt ttg gtt gca           4227
Tyr Trp Ala Cys Pro  Val Ala Trp Thr Leu  Tyr Gly Leu Val Ala
         1355                1360                1365 tct caa ttt gga gac  ctc caa gat aca att  aat gat caa act gtg           4272
Ser Gln Phe Gly Asp  Leu Gln Asp Thr Ile  Asn Asp Gln Thr Val
         1370                1375                1380 gaa gat ttc ttg aga  agt agc tat gga ttt  aag cat gat ttt cta           4317
Glu Asp Phe Leu Arg  Ser Ser Tyr Gly Phe  Lys His Asp Phe Leu
         1385                1390                1395 gga gtt gtt gca gct  gtg atc gtt gca ttt  gca gtt gtt ttc gcc           4362
Gly Val Val Ala Ala  Val Ile Val Ala Phe  Ala Val Val Phe Ala
         1400                1405                1410 ttc aca ttt gct ttg  ggt atc aag gca ttc  aat ttc cag aga aga           4407
Phe Thr Phe Ala Leu  Gly Ile Lys Ala Phe  Asn Phe Gln Arg Arg
         1415                1420                1425 tagaaatagt atttatttgt attcccagtt gttcatatat tcttgaataa gcttatgaag       4467
```

```
ttttaagtta ctgaatatgt tatgtcttac taatctttct caattcccag ttttgttgta    4527
taataacatg taataattgt tattcaaaaa aaaaaaaaaa aaaa                     4571
```

<210> SEQ ID NO 2
<211> LENGTH: 1425
<212> TYPE: PRT
<213> ORGANISM: Hyoscyamus muticus

<400> SEQUENCE: 2

```
Met Glu Pro Ser Asp Leu Ser Asn Phe Arg Gly Arg Ser Met Arg Gly
1               5                   10                  15

Ser Met Arg Gly Ser Val Arg Glu Asn Ser Asn Ser Ile Trp Arg Asn
            20                  25                  30

Asn Gly Val Glu Ile Phe Ser Arg Ser Thr Arg Asp Glu Asp Asp Glu
        35                  40                  45

Glu Ala Leu Lys Trp Ala Ala Leu Glu Lys Leu Pro Thr Tyr Asp Arg
    50                  55                  60

Leu Arg Lys Gly Ile Leu Phe Gly Ser Gln Gly Thr Gly Val Ala Glu
65                  70                  75                  80

Val Asp Val Asp Leu Gly Val Gln Gln Arg Lys Asn Leu Leu Asp
                85                  90                  95

Arg Leu Val Lys Ile Ala Glu Glu Asp Asn Glu Lys Phe Leu Leu Lys
            100                 105                 110

Leu Lys Asn Arg Ile Asp Arg Val Gly Ile Asp Phe Pro Ser Ile Glu
        115                 120                 125

Val Arg Phe Glu His Leu Asn Ile Glu Ala Asp Ala Tyr Val Gly Ser
    130                 135                 140

Arg Ala Leu Pro Thr Phe Thr Asn Phe Ile Ser Asn Phe Ile Glu Ser
145                 150                 155                 160

Leu Leu Asp Ser Leu His Ile Leu Pro Ser Lys Lys Arg Ser Val Thr
                165                 170                 175

Ile Leu Lys Asp Val Ser Gly Ile Val Lys Pro Cys Arg Met Thr Leu
            180                 185                 190

Leu Leu Gly Pro Pro Gly Ser Gly Lys Thr Thr Leu Leu Leu Ala Leu
        195                 200                 205

Ala Gly Lys Leu Asp Ser Ala Leu Arg Val Thr Gly Lys Val Thr Tyr
    210                 215                 220

Asn Gly His Glu Leu His Glu Phe Val Pro Gln Arg Thr Ala Ala Tyr
225                 230                 235                 240

Ile Ser Gln His Asp Leu His Ile Gly Glu Met Thr Val Arg Glu Thr
                245                 250                 255

Leu Glu Phe Ser Ala Arg Cys Gln Gly Val Gly Ser Arg Tyr Glu Met
            260                 265                 270

Leu Ala Glu Leu Ser Arg Arg Glu Lys Ala Ala Asn Ile Lys Pro Asp
        275                 280                 285

Ala Asp Ile Asp Met Phe Met Lys Ala Ala Ser Thr Glu Gly Gln Glu
    290                 295                 300

Ala Lys Val Ile Thr Asp Tyr Val Leu Lys Ile Leu Gly Leu Asp Ile
305                 310                 315                 320

Cys Ala Asp Thr Met Val Gly Asp Gln Met Ile Arg Gly Ile Ser Gly
                325                 330                 335

Gly Gln Lys Lys Arg Val Thr Thr Gly Glu Met Ile Val Gly Pro Ser
            340                 345                 350
```

-continued

```
Lys Ala Leu Phe Met Asp Glu Ile Ser Thr Gly Leu Asp Ser Ser Thr
            355                 360                 365

Thr Tyr Ser Ile Val Asn Ser Leu Lys Gln Ser Val Gln Ile Leu Lys
    370                 375                 380

Gly Thr Ala Leu Ile Ser Leu Leu Gln Pro Ala Pro Glu Thr Tyr Asn
385                 390                 395                 400

Leu Phe Asp Asp Ile Val Leu Leu Ser Asp Gly Tyr Ile Val Tyr Gln
                405                 410                 415

Gly Pro Arg Glu Glu Val Leu Asp Phe Phe Glu Ser Met Gly Phe Lys
            420                 425                 430

Cys Pro Asn Arg Lys Gly Val Ala Asp Phe Leu Gln Glu Val Thr Ser
            435                 440                 445

Lys Lys Asp Gln Gln Gln Tyr Trp Val Lys Arg Asp Glu Pro Tyr Arg
    450                 455                 460

Phe Ile Thr Ser Lys Glu Phe Ala Glu Ala Tyr Gln Ser Phe His Val
465                 470                 475                 480

Gly Arg Lys Val Ser Asp Glu Leu Thr Thr Ala Phe Asp Lys Ser Lys
                485                 490                 495

Ser His Pro Ala Ala Leu Thr Thr Glu Lys Tyr Gly Ile Gly Val Lys
            500                 505                 510

Gln Leu Leu Lys Val Cys Thr Glu Arg Glu Phe Leu Leu Met Gln Arg
            515                 520                 525

Asn Ser Phe Val Tyr Ile Phe Lys Phe Phe Gln Leu Met Val Ile Ala
    530                 535                 540

Leu Met Thr Met Thr Ile Phe Phe Arg Thr Lys Met Ser Arg Asp Thr
545                 550                 555                 560

Glu Thr Asp Gly Gly Ile Tyr Ser Gly Ala Leu Phe Phe Thr Val Val
                565                 570                 575

Met Leu Met Phe Asn Gly Leu Ser Glu Leu Pro Leu Thr Leu Tyr Lys
            580                 585                 590

Leu Pro Val Phe Tyr Lys Gln Arg Asp Phe Leu Phe Tyr Pro Ser Trp
            595                 600                 605

Ala Tyr Ala Val Pro Ser Trp Ile Leu Lys Ile Pro Val Thr Phe Leu
    610                 615                 620

Glu Val Gly Met Trp Val Phe Leu Thr Tyr Tyr Val Ile Gly Phe Asp
625                 630                 635                 640

Pro Asn Val Gly Arg Phe Phe Lys Gln Phe Leu Leu Leu Ile Val Val
                645                 650                 655

Asn Gln Met Ala Ser Gly Leu Phe Arg Phe Ile Ala Ala Val Gly Arg
            660                 665                 670

Thr Met Gly Val Ala Ser Thr Phe Gly Ala Phe Ala Leu Leu Leu Gln
            675                 680                 685

Phe Ala Leu Gly Gly Phe Val Leu Ala Arg Thr Asp Val Lys Asp Trp
    690                 695                 700

Trp Ile Trp Gly Tyr Trp Thr Ser Pro Leu Met Phe Ser Val Asn Ala
705                 710                 715                 720

Ile Leu Val Asn Glu Phe Asp Gly Lys Lys Trp Lys His Ile Ala Pro
                725                 730                 735

Asn Gly Thr Glu Pro Leu Gly Pro Ala Val Val Arg Ser Gln Gly Phe
            740                 745                 750

Phe Pro Asp Ala Tyr Trp Tyr Trp Ile Gly Val Gly Ala Leu Val Gly
            755                 760                 765

Phe Thr Val Leu Phe Asn Ile Ala Tyr Ser Leu Ala Leu Ala Tyr Leu
```

-continued

```
            770                 775                 780
Asn Pro Phe Gly Lys Pro Gln Ala Thr Ile Ser Glu Glu Ser Glu Ser
785                 790                 795                 800

Asn Glu Asn Ser Glu Leu Ser Thr Pro Ile Ala Ser Thr Thr Glu Gly
                805                 810                 815

Asp Ser Val Gly Glu Asn Gln Asn Lys Lys Gly Met Val Leu Pro Phe
                820                 825                 830

Glu Pro His Ser Ile Thr Phe Asp Glu Val Val Tyr Ser Val Asp Met
                835                 840                 845

Pro Pro Glu Met Arg Glu Gln Gly Thr Ser Asp Asn Arg Leu Val Leu
                850                 855                 860

Leu Lys Ser Val Ser Gly Ala Phe Arg Pro Gly Val Leu Thr Ala Leu
865                 870                 875                 880

Met Gly Val Ser Gly Ala Gly Lys Thr Thr Leu Met Asp Val Leu Ala
                885                 890                 895

Gly Arg Lys Thr Gly Gly Tyr Ile Asp Gly Ser Ile Asn Ile Ser Gly
                900                 905                 910

Tyr Pro Lys Lys Gln Glu Thr Phe Ala Arg Ile Ser Gly Tyr Cys Glu
                915                 920                 925

Gln Asn Asp Ile His Ser Pro Tyr Val Thr Val Tyr Glu Ser Leu Val
                930                 935                 940

Tyr Ser Ala Trp Leu Arg Leu Pro Gln Asp Val Asp Glu Lys Lys Arg
945                 950                 955                 960

Met Met Phe Val Glu Gln Val Met Glu Leu Val Glu Leu Thr Pro Leu
                965                 970                 975

Arg Ser Ala Leu Val Gly Leu Pro Gly Val Asn Gly Leu Thr Ile Ala
                980                 985                 990

Val Glu Leu Val Ala Asn Pro Ser Ile Ile Phe Met Asp Glu Pro Thr
                995                1000                1005

Ser Gly Leu Asp Ala Arg Ala Ala Ala Ile Val Met Arg Ala Val
                1010                1015                1020

Arg Asn Thr Val Asp Thr Gly Arg Thr Val Val Cys Thr Ile His
                1025                1030                1035

Gln Pro Ser Ile Asp Ile Phe Glu Ala Phe Asp Glu Leu Phe Leu
                1040                1045                1050

Met Lys Arg Gly Gly Gln Glu Ile Tyr Val Gly Pro Leu Gly Arg
                1055                1060                1065

Glu Ser Ser His Leu Ile Lys Tyr Phe Glu Ser Ile Pro Gly Val
                1070                1075                1080

Thr Lys Ile Lys Glu Gly Tyr Asn Pro Ala Thr Trp Met Leu Glu
                1085                1090                1095

Val Thr Ser Ser Ser Gln Glu Ile Thr Leu Gly Val Asp Phe Thr
                1100                1105                1110

Glu Leu Tyr Lys Asn Ser Asp Leu Phe Arg Arg Asn Lys Ala Leu
                1115                1120                1125

Ile Glu Glu Leu Ser Val Pro Arg Pro Gly Thr Ser Asp Leu His
                1130                1135                1140

Phe Glu Thr Glu Phe Ser Gln Pro Phe Trp Val Gln Cys Met Ala
                1145                1150                1155

Cys Leu Trp Lys Gln His Trp Ser Tyr Trp Arg Asn Pro Ala Tyr
                1160                1165                1170

Thr Ala Val Arg Phe Leu Phe Thr Thr Phe Ile Ala Leu Ile Phe
                1175                1180                1185
```

```
Gly Ser Met Phe Trp Asp Ile Gly Thr Lys Val Ser Gly Pro Gln
    1190                1195                1200

Asp Leu Lys Asn Ala Met Gly Ser Met Tyr Ala Ala Val Leu Phe
    1205                1210                1215

Leu Gly Val Gln Asn Ser Ser Ser Val Gln Pro Val Val Ser Val
    1220                1225                1230

Glu Arg Thr Val Phe Tyr Arg Glu Lys Ala Ala Gly Met Tyr Ser
    1235                1240                1245

Ala Met Pro Tyr Ala Phe Ala Gln Val Phe Ile Glu Ile Pro Tyr
    1250                1255                1260

Val Phe Val Gln Ala Val Val Tyr Gly Leu Ile Val Tyr Ser Met
    1265                1270                1275

Ile Gly Phe Glu Trp Thr Ala Ala Lys Phe Phe Trp Tyr Phe Phe
    1280                1285                1290

Phe Met Phe Phe Thr Phe Leu Tyr Phe Thr Phe Phe Gly Met Met
    1295                1300                1305

Thr Val Ala Val Thr Pro Asn Gln Asn Val Ala Ser Ile Val Ala
    1310                1315                1320

Gly Phe Phe Tyr Thr Val Trp Asn Leu Phe Ser Gly Phe Ile Val
    1325                1330                1335

Pro Arg Pro Arg Ile Pro Ile Trp Trp Arg Trp Tyr Tyr Trp Ala
    1340                1345                1350

Cys Pro Val Ala Trp Thr Leu Tyr Gly Leu Val Ala Ser Gln Phe
    1355                1360                1365

Gly Asp Leu Gln Asp Thr Ile Asn Asp Gln Thr Val Glu Asp Phe
    1370                1375                1380

Leu Arg Ser Ser Tyr Gly Phe Lys His Asp Phe Leu Gly Val Val
    1385                1390                1395

Ala Ala Val Ile Val Ala Phe Ala Val Phe Ala Phe Thr Phe
    1400                1405                1410

Ala Leu Gly Ile Lys Ala Phe Asn Phe Gln Arg Arg
    1415                1420                1425

<210> SEQ ID NO 3
<211> LENGTH: 40
<212> TYPE: DNA
<213> ORGANISM: Artificial Sequence
<220> FEATURE:
<223> OTHER INFORMATION: forward primer in example 3.1

<400> SEQUENCE: 3
aaaaagcagg ctaccatgcc cgaggccaag cttaacaata                            40

<210> SEQ ID NO 4
<211> LENGTH: 40
<212> TYPE: DNA
<213> ORGANISM: Artificial Sequence
<220> FEATURE:
<223> OTHER INFORMATION: reverse primer of example 3.1

<400> SEQUENCE: 4
agaaagctgg gtccatcttg gtaagtttct tttcttaacc                            40

<210> SEQ ID NO 5
<211> LENGTH: 37
<212> TYPE: PRT
<213> ORGANISM: Ipomoea batatas
<300> PUBLICATION INFORMATION:
```

<301> AUTHORS: Matsuoka and Nakamura
<302> TITLE: Propeptide of a precursor to a plant vacuolar protein
       required for vacuolar targeting
<303> JOURNAL: Proc. Natl. Acad. Sci. USA
<304> VOLUME: 88
<305> ISSUE: 3
<306> PAGES: 834-8
<307> DATE: 1991-02-01
<308> DATABASE ACCESSION NUMBER: PMID: 1992474
<309> DATABASE ENTRY DATE: 1991-02-01
<313> RELEVANT RESIDUES: (1)..(37)

<400> SEQUENCE: 5

Met Lys Ala Phe Thr Leu Ala Leu Phe Leu Ala Leu Ser Leu Tyr Leu
1               5                   10                  15

Leu Pro Asn Pro Ala His Ser Arg Phe Asn Pro Ile Arg Leu Pro Thr
            20                  25                  30

Thr His Glu Pro Ala
        35

<210> SEQ ID NO 6
<211> LENGTH: 12
<212> TYPE: PRT
<213> ORGANISM: Nicotiana tabacum
<300> PUBLICATION INFORMATION:
<301> AUTHORS: Neuhaus, J.M.; Sticher, L.; Meins, F. and Boller, T.
<302> TITLE: A short C-terminal sequence is necessary and sufficient for
       the targeting of chitinases to the plant vacuole
<303> JOURNAL: Proc. Natl. Acad. Sci. USA
<304> VOLUME: 88
<305> ISSUE: 22
<306> PAGES: 10362-10366
<307> DATE: 1991-11-15
<308> DATABASE ACCESSION NUMBER: PMID: 1946457
<309> DATABASE ENTRY DATE: 1991-11-25
<313> RELEVANT RESIDUES: (318)..(329)

<400> SEQUENCE: 6

Asp Leu Leu Gly Asn Gly Leu Leu Val Asp Thr Met
1               5                   10

<210> SEQ ID NO 7
<211> LENGTH: 34
<212> TYPE: DNA
<213> ORGANISM: Artificial Sequence
<220> FEATURE:
<223> OTHER INFORMATION: forward primer in example 5.1

<400> SEQUENCE: 7
aaaaagcagg ctaccatgga gacgttatcg agaa                              34

<210> SEQ ID NO 8
<211> LENGTH: 34
<212> TYPE: DNA
<213> ORGANISM: Artificial Sequence
<220> FEATURE:
<223> OTHER INFORMATION: reverse primer in example 5.1

<400> SEQUENCE: 8
agaaagctgg gtctatcgtt gttggaagtt gagc                              34

<210> SEQ ID NO 9
<211> LENGTH: 12789
<212> TYPE: DNA
<213> ORGANISM: Artificial Sequence
<220> FEATURE:
<223> OTHER INFORMATION: vector pK7WG2D
<220> FEATURE:
<221> NAME/KEY: misc_feature
<222> LOCATION: (4772)..(4772)
<223> OTHER INFORMATION: n can be any base

<400> SEQUENCE: 9

| | | | | | |
|---|---|---|---|---|---|
| tgatcacagg | cagcaacgct | ctgtcatcgt | tacaatcaac | atgctaccct | ccgcgagatc | 60 |
| atccgtgttt | caaacccggc | agcttagttg | ccgttcttcc | gaatagcatc | ggtaacatga | 120 |
| gcaaagtctg | ccgccttaca | acggctctcc | cgctgacgcc | gtcccggact | gatgggctgc | 180 |
| ctgtatcgag | tggtgatttt | gtgccgagct | gccggtcggg | gagctgttgg | ctggctggtg | 240 |
| gcaggatata | ttgtggtgta | aacaaattga | cgcttagaca | acttaataac | acattgcgga | 300 |
| cgtttttaat | gtactgaatt | aacgccgaat | tgaattatca | gcttgcatgc | cggtcgatct | 360 |
| agtaacatag | atgacaccgc | gcgcgataat | ttatcctagt | ttgcgcgcta | tattttgttt | 420 |
| tctatcgcgt | attaaatgta | taattgcggg | actctaatca | aaaacccat | ctcataaata | 480 |
| acgtcatgca | ttcatgtta | attattacat | gcttaacgta | attcaacaga | aattatatga | 540 |
| taatcatcgc | aagaccggca | acaggattca | atcttaagaa | actttattgc | caaatgtttg | 600 |
| aacgatctgc | ttgactctag | ctagagtccg | aaccccagag | tcccgctcag | aagaactcgt | 660 |
| caagaaggcg | atagaaggcg | atgcgctgcg | aatcgggagc | ggcgataccg | taaagcacga | 720 |
| ggaagcggtc | agcccattcg | ccgccaagct | cttcagcaat | atcacgggta | gccaacgcta | 780 |
| tgtcctgata | gcggtccgcc | acaccagcc | ggccacagtc | gatgaatcca | gaaaagcggc | 840 |
| cattttccac | catgatattc | ggcaagcagg | catcgccctg | ggtcacgacg | agatcctcgc | 900 |
| cgtcgggcat | ccgcgccttg | agcctggcga | acagttcggc | tggcgcgagc | ccctgatgct | 960 |
| cttcgtccag | atcatcctga | tcgacaagac | cggcttccat | ccgagtacgt | cctcgctcga | 1020 |
| tgcgatgttt | cgcttggtgg | tcgaatgggc | aggtagccgg | atcaagcgta | tgcagccgcc | 1080 |
| gcattgcatc | agccatgatg | gatactttct | cggcaggagc | aaggtgagat | gacaggagat | 1140 |
| cctgccccgg | cacttcgccc | aatagcagcc | agtcccttcc | cgcttcagtg | acaacgtcga | 1200 |
| gcacagctgc | gcaaggaacg | cccgtcgtgg | ccagccacga | tagccgcgct | gcctcgtctt | 1260 |
| ggagttcatt | cagggcaccg | gacaggtcgg | tcttgacaaa | agaaccggg | cgcccctgcg | 1320 |
| ctgacagccg | gaacacggcg | gcatcagagc | agccgattgt | ctgttgtgcc | cagtcatagc | 1380 |
| cgaatagcct | ctccacccaa | gcggccgag | aacctgcgtg | caatccatct | tgttcaatca | 1440 |
| tgcctcgatc | gagttgagag | tgaatatgag | actctaattg | gataccgagg | ggaatttatg | 1500 |
| gaacgtcagt | ggagcatttt | tgacaagaaa | tatttgctag | ctgatagtga | ccttaggcga | 1560 |
| cttttgaacg | cgcaataatg | gtttctgacg | tatgtgctta | gctcattaaa | ctccagaaac | 1620 |
| ccgcggctga | gtggctcctt | caacgttgcg | gttctgtcag | ttccaaacgt | aaaacggctt | 1680 |
| gtcccgcgtc | atcggcgggg | gtcataacgt | gactcccta | attctcatgt | atgataattc | 1740 |
| gcggtacccg | gggatcctct | agagggcccg | acgtcgcatg | cctgcaggtc | actgacttttt | 1800 |
| ggttttagga | attagaaatt | ttattgatag | aagtatttta | caaatacaaa | tacatactaa | 1860 |
| gggtttctta | tatgctcaac | acatgagcga | aaccctataa | gaaccctaat | tcccttatct | 1920 |
| gggaactact | cacacattat | tctggagaaa | aatagagaga | gatagatttg | tagagagaga | 1980 |
| ctggtgattt | tgcggactc | tagcatggcc | gcgggatatc | accactttgt | acaagaaagc | 2040 |
| tgaacgagaa | acgtaaaatg | atataaatat | caatatatta | aattagattt | tgcataaaaa | 2100 |
| acagactaca | taatactgta | aaacacaaca | tatccagtca | ctatggtcga | cctgcagact | 2160 |
| ggctgtgtat | aagggagcct | gacatttata | ttccccagaa | catcaggtta | atggcgtttt | 2220 |

```
tgatgtcatt ttcgcggtgg ctgagatcag ccacttcttc cccgataacg gagaccggca    2280
cactggccat atcggtggtc atcatgcgcc agctttcatc cccgatatgc accaccgggt    2340
aaagttcacg ggagacttta tctgacagca gacgtgcact ggccaggggg atcaccatcc    2400
gtcgcccggg cgtgtcaata atatcactct gtacatccac aaacagacga taacggctct    2460
ctcttttata ggtgtaaacc ttaaactgca tttcaccagt ccctgttctc gtcagcaaaa    2520
gagccgttca tttcaataaa ccgggcgacc tcagccatcc cttcctgatt ttccgctttc    2580
cagcgttcgg cacgcagacg acgggcttca ttctgcatgg ttgtgcttac cagaccggag    2640
atattgacat catatatgcc ttgagcaact gatagctgtc gctgtcaact gtcactgtaa    2700
tacgctgctt catagcacac ctctttttga catacttcgg gtatacatat cagtatatat    2760
tcttataccg caaaaatcag cgcgcaaata cgcatactgt tatctggctt ttagtaagcc    2820
ggatccacgc gtttacgccc cgccctgcca ctcatcgcag tactgttgta attcattaag    2880
cattctgccg acatggaagc catcacagac ggcatgatga acctgaatcg ccagcggcat    2940
cagcaccttg tcgccttgcg tataatattt gcccatggtg aaaacggggg cgaagaagtt    3000
gtccatattg gccacgttta aatcaaaact ggtgaaactc acccagggat tggctgagac    3060
gaaaaacata ttctcaataa acccttaggg aaataggcc aggttttcac cgtaacacgc    3120
cacatcttgc gaatatatgt gtagaaactg ccggaaatcg tcgtggtatt cactccagag    3180
cgatgaaaac gtttcagttt gctcatggaa aacggtgtaa caagggtgaa cactatccca    3240
tatcaccagc tcaccgtctt tcattgccat acgaattcc ggatgagcat tcatcaggcg    3300
ggcaagaatg tgaataaagg ccggataaaa cttgtgctta ttttttcttta cggtctttaa    3360 aaaggccgta atatccagct gaacggtctg gttataggta cattgagcaa ctgactgaaa    3420
tgcctcaaaa tgttctttac gatgccattg ggatatatca acggtggtat atccagtgat    3480 tttttttctcc atttttagctt ccttagctcc tgaaaatctc gccggatcct aactcaaaat    3540
ccacacatta tacgagccgg aagcataaag tgtaaagcct ggggtgccta atgcggccgc    3600
catagtgact ggatatgttg tgttttacag tattatgtag tctgttttt atgcaaaatc    3660 taatttaata tattgatatt tatatcattt tacgtttctc gttcagcttt tttgtacaaa    3720
cttgtgatat cactagtgcg gccgcctgca ggtcgactag aatagtaaat tgtaatgttg    3780
tttgttgttt gttttgttgt ggtaattgtt gtaaaaatac ggatcgtcct gcagtcctct    3840
ccaaatgaaa tgaacttcct tatatagagg aagggtcttg cgaaggatag tgggattgtg    3900
cgtcatccct tacgtcagtg gagatatcac atcaatccac ttgctttgaa gacgtggttg    3960
gaacgtcttc ttttttccacg atgctcctcg tgggtggggg tccatctttg ggaccactgt    4020
cggcagaggc atcttgaacg atagcctttc ctttatcgca atgatggcat ttgtaggtgc    4080
caccttcctt ttctactgtc cttttgatga agtgacagat agctgggcaa tggaatccga    4140
ggaggtttcc cgatattacc ctttgttgaa aagtctcaat agcccttgg tcttctgaga    4200 ctgtatcttt gatattcttg gagtagacga gagtgtcgtg ctccaccatg ttgacgaaga    4260
ttttcttctt gtcattgagt cgtaaaagac tctgtatgaa ctgttcgcca gtcttcacgg    4320
cgagttctgt tagatcctcg atctgaattt ttgactccat ggcctttgat tcagtaggaa    4380
ctactttctt agagactcca atctctatta cttgccttgg tttatgaagc aagccttgaa    4440
tcgtccatac tggaatagta cttctgatct tgagaaatat atctttctct gtgttcttga    4500
tgcagttagt cctgaatctt ttgactgcat ctttaacctt cttgggaagg tatttgatct    4560
cctggagatt attactcggg tagatcgtct tgatgagacc tgccgcgtag gcctctctaa    4620
```

```
ccatctgtgg gtcagcattc tttctgaaat tgaagaggct aatcttctca ttatcggtgg    4680
tgaacatggt atcgtcacct tctccgtcga actttcttcc tagatcgtag agatagagaa    4740
agtcgtccat ggtgatctcc ggggcaaagg anatctcgac catatgggag agctcaagct    4800
tgcatgcctg caggtcactg gattttggtt ttaggaatta gaaattttat tgatagaagt    4860
attttacaaa tacaaataca tactaagggt ttcttatatg ctcaacacat gagcgaaacc    4920
ctataagaac cctaattccc ttatgtggga actactcaca cattattctg gagaaaaata    4980
gagagagata gatttgtaga gagagactgg tgatttttgc ggactctaga actagtggat    5040
cccccgggct gcagccgggc ggcgcttaca gctcgtcctt cttgtacagc tcgtccatgc    5100
cgagagtgat cccggcggcg gtcacgaact ccagcaggac catgtgatcg cgcttctcgt    5160
tggggtcttt gctcagggcg gactgggtgc tcaggtagtg gttgtcgggc agcagcacgg    5220
ggccgtcgcc gatgggggtg ttctgctggt agtggtcggc gagctgcacg ctgccgtcct    5280
cgatgttgtg gcggatcttg aagttcacct tgatgccgtt cttctgcttg tcggccatga    5340
tatagacgtt gtggctgttg tagttgtact ccagcttgtg ccccaggatg ttgccgtcct    5400
ccttgaagtc gatgcccttc agctcgatgc ggttcaccag ggtgtcgccc tcgaacttca    5460
cctcggcgcg ggtcttgtag ttgccgtcgt ccttgaagaa gatggtgcgc tcctggacgt    5520
agccttcggg catggcggac ttgaagaagt cgtgctgctt catgtggtcg gggtagcggc    5580
tgaagcactg cacgccgtag gtcagggtgg tcacgagggt gggccagggc acggcagct    5640
tgccggtggt gcagatgaac ttcagggtca gcttgccgta ggtggcatcg ccctcgcct    5700
cgccggacac gctgaacttg tggccgttta cgtcgccgtc cagctcgacc aggatgggca    5760
ccaccccggt gaacagctcc tcgcccttgc tcaccatgtc ggccgaggat aatgatagga    5820
gaagtgaaaa gatgaaaaag agaaaaagat tagtcttcac catggctatc gttcgtaaat    5880
ggtgaaaatt ttcagaaaat agcttttgct ttaaaagaaa tgatttaaat tgctgcaata    5940
gaagtagaat gcttgattgc ttgagattcg tttgttttgt atatgttgtg ttgagaattc    6000
gagctcggta cccggggatc ctctagcgaa ttttctctgc tcaaattgtt gaggttagcg    6060
gatttgtaaa cgcgtttata tgggctgctt ggagggtact tttggattaa ttttttttctg    6120
ccagcgcatt ctgacgcggc accgctttgg aaagtgcgct gtgggtccgc gttttctaca    6180
ataatgtgcc gatccggtca gaaagtatat ggatgagttg tgccagcctc accaacgtgc    6240
tgcaggccca tcatgactac ttcaatgtta atgggggtaa tgaataaata ggcgaaattg    6300
ggttcacggt gggcccaggg aatataatat tgccgcagag gtagtcggat gccaaggccc    6360
gcaactaata gttcacgaac aaattcctag agagtcgacc tgcagcatgc aagctaacct    6420
gcaggcatgc aagcttagct tgagcttgga tcagattgtc gtttcccgcc ttcagtttaa    6480
actatcagtg tttgacagga tatattggcg ggtaaaccta agagaaaaga gcgtttatta    6540
gaataacgga tatttaaaag ggcgtgaaaa ggtttatccg ttcgtccatt tgtatgtgca    6600
tgccaaccac agggttcccc tcgggatcaa agtactttga tccaacccct ccgctgctat    6660
agtgcagtcg gcttctgacg ttcagtgcag ccgtcttctg aaaacgacat gtcgcacaag    6720
tcctaagtta cgcgacaggc tgccgccctg ccctttttcct ggcgttttct tgtcgcgtgt    6780
tttagtcgca taaagtagaa tacttgcgac tagaaccgga gacattacgc catgaacaag    6840
agcgccgccg ctggcctgct gggctatgcc cgcgtcagca ccgacgacca ggacttgacc    6900
aaccaacggg ccgaactgca cgcggccggc tgcaccaagc tgttttccga agagatcacc    6960
```

```
ggcaccaggc gcgaccgccc ggagctggcc aggatgcttg accacctacg ccctggcgac    7020
gttgtgacag tgaccaggct agaccgcctg gcccgcagca cccgcgacct actggacatt    7080
gccgagcgca tccaggaggc cggcgcgggc ctgcgtagcc tggcagagcc gtgggccgac    7140
accaccacgc cggccggccg catggtgttg accgtgttcg ccggcattgc cgagttcgag    7200
cgttccctaa tcatcgaccg cacccggagc gggcgcgagg ccgccaaggc ccgaggcgtg    7260
aagtttggcc cccgccctac cctcaccccg gcacagatcg cgcacgcccg cgagctgatc    7320
gaccaggaag ccgcaccgt gaaagaggcg gctgcactgc ttggcgtgca tcgctcgacc     7380
ctgtaccgcg cacttgagcg cagcgaggaa gtgacgccca ccgaggccag gcggcgcggt    7440
gccttccgtg aggacgcatt gaccgaggcc gacgccctgg cggccgccga aatgaacgc     7500 caagaggaac aagcatgaaa ccgcaccagg acggccagga cgaaccgttt ttcattaccg    7560
aagagatcga ggcggagatg atcgcggccg ggtacgtgtt cgagccgccc gcgcacgtct    7620
caaccgtgcg gctgcatgaa atcctggccg gtttgtctga tgccaagctg gcggcctggc    7680
cggccagctt ggccgctgaa gaaaccgagc gccgccgtct aaaaaggtga tgtgtatttg    7740
agtaaaacag cttgcgtcat gcggtcgctg cgtatatgat gcgatgagta aataaacaaa    7800
tacgcaaggg gaacgcatga aggttatcgc tgtacttaac cagaaaggcg ggtcaggcaa    7860
gacgaccatc gcaacccatc tagcccgcgc cctgcaactc gccggggccg atgttctgtt    7920
agtcgattcc gatccccagg gcagtgcccg cgattgggcg ccgtgcggg aagatcaacc     7980 gctaaccgtt gtcggcatcg accgcccgac gattgaccgc gacgtgaagg ccatcggccg    8040
gcgcgacttc gtagtgatcg acggagcgcc ccaggcggcg gacttggctg tgtccgcgat    8100
caaggcagcc gacttcgtgc tgattccggt gcagccaagc ccttacgaca tatgggccac    8160
cgccgacctg gtggagctgg ttaagcagcg cattgaggtc acggatggaa ggctacaagc    8220
ggcctttgtc gtgtcgcggg cgatcaaagg cacgcgcatc ggcggtgagg ttgccgaggc    8280
gctggccggg tacgagctgc ccattcttga gtcccgtatc acgcagcgcg tgagctaccc    8340
aggcactgcc gccgccggca caaccgttct tgaatcagaa cccgagggcg acgctgcccg    8400
cgaggtccag gcgctggccg ctgaaattaa atcaaaactc atttgagtta atgaggtaaa    8460
gagaaaatga gcaaaagcac aaacacgcta agtgccggcc gtccgagcgc acgcagcagc    8520
aaggctgcaa cgttggccag cctggcagac acgccagcca tgaagcgggt caactttcag    8580
ttgccggcgg aggatcacac caagctgaag atgtacgcgg tacgccaagg caagaccatt    8640
accgagctgc tatctgaata catcgcgcag ctaccagagt aaatgagcaa atgaataaat    8700
gagtagatga attttagcgg ctaaaggagg cggcatggaa atcaagaac aaccaggcac     8760 cgacgccgtg gaatgcccca tgtgtggagg aacgggcggt tggccaggcg taagcggctg    8820
ggttgtctgc cggccctgca atggcactgg aaccccaag cccgaggaat cggcgtgacg     8880
gtcgcaaacc atccggcccg gtacaaatcg cgcggcgct gggtgatgac ctggtggaga    8940
agttgaaggc cgcgcaggcc gcccagcggc aacgcatcga ggcagaagca cgccccggtg    9000
aatcgtggca agcggccgct gatcgaatcc gcaaagaatc ccggcaaccg ccggcagccg    9060
gtgcgccgtc gattaggaag ccgcccaagg gcgacgagca accagatttt ttcgttccga    9120
tgctctatga cgtgggcacc cgcgatagtg cagcatcat ggacgtggcc gttttccgtc     9180
tgtcgaagcg tgaccgacga gctggcgagg tgatccgcta cgagcttcca gacgggcacg    9240
tagaggtttc cgcagggccg gccggcatgg ccagtgtgtg ggattacgac ctggtactga    9300
tggcggtttc ccatctaacc gaatccatga accgataccg ggaagggaag ggagacaagc    9360
```

```
ccggccgcgt gttccgtcca cacgttgcgg acgtactcaa gttctgccgg cgagccgatg    9420
gcggaaagca gaaagacgac ctggtagaaa cctgcattcg gttaaacacc acgcacgttg    9480
ccatgcagcg tacgaagaag gccaagaacg gccgcctggt gacggtatcc gagggtgaag    9540
ccttgattag ccgctacaag atcgtaaaga gcgaaaccgg gcggccggag tacatcgaga    9600
tcgagctagc tgattggatg taccgcgaga tcacagaagg caagaacccg gacgtgctga    9660
cggttcaccc cgattacttt ttgatcgatc ccggcatcgg ccgttttctc taccgcctgg    9720
cacgccgcgc cgcaggcaag gcagaagcca gatggttgtt caagacgatc tacgaacgca    9780
gtggcagcgc cggagagttc aagaagttct gtttcaccgt gcgcaagctg atcgggtcaa    9840
atgacctgcc ggagtacgat ttgaaggagg aggcggggca ggctggcccg atcctagtca    9900
tgcgctaccg caacctgatc gagggcgaag catccgccgg ttcctaatgt acggagcaga    9960
tgctagggca aattgcccta gcaggggaaa aaggtcgaaa aggtctcttt cctgtggata   10020
gcacgtacat tgggaaccca aagccgtaca ttgggaaccg gaacccgtac attgggaacc   10080
caaagccgta cattgggaac cggtcacaca tgtaagtgac tgatataaaa gagaaaaaag   10140 gcgattttc cgcctaaaac tctttaaaac ttattaaaac tcttaaaacc cgcctggcct   10200
gtgcataact gtctggccag cgcacagccg aagagctgca aaaagcgcct acccttcggt   10260
cgctgcgctc cctacgcccc gccgcttcgc gtcggcctat cgcggccgct ggccgctcaa   10320
aaatggctgg cctacggcca ggcaatctac cagggcgcgg acaagccgcg ccgtcgccac   10380
tcgaccgccg gcgcccacat caaggcaccc tgcctcgcgc gtttcggtga tgacggtgaa   10440
aacctctgac acatgcagct cccggagacg gtcacagctt gtctgtaagc ggatgccggg   10500
agcagacaag cccgtcaggg cgcgtcagcg ggtgttggcg ggtgtcgggg cgcagccatg   10560
acccagtcac gtagcgatag cggagtgtat actggcttaa ctatgcggca tcagagcaga   10620
ttgtactgag agtgcaccat atgcggtgtg aaataccgca cagatgcgta aggagaaaat   10680
accgcatcag gcgctcttcc gcttcctcgc tcactgactc gctgcgctcg gtcgttcggc   10740
tgcggcgagc ggtatcagct cactcaaagg cggtaatacg gttatccaca gaatcagggg   10800
ataacgcagg aaagaacatg tgagcaaaag gccagcaaaa ggccaggaac cgtaaaaagg   10860
ccgcgttgct ggcgtttttc cataggctcc gcccccctga cgagcatcac aaaaatcgac   10920
gctcaagtca gaggtggcga aacccgacag gactataaag ataccaggcg tttccccctg   10980
gaagctccct cgtgcgctct cctgttccga ccctgccgct taccggatac ctgtccgcct   11040
ttctcccttc gggaagcgtg gcgctttctc atagctcacg ctgtaggtat ctcagttcgg   11100
tgtaggtcgt tcgctccaag ctgggctgtg tgcacgaacc ccccgttcag cccgaccgct   11160
gcgccttatc cggtaactat cgtcttgagt ccaacccggt aagacacgac ttatcgccac   11220
tggcagcagc cactggtaac aggattagca gagcgaggta tgtaggcggt gctacagagt   11280
tcttgaagtg gtggcctaac tacggctaca ctagaaggac agtatttggt atctgcgctc   11340
tgctgaagcc agttaccttc ggaaaaagag ttggtagctc ttgatccggc aaacaaacca   11400
ccgctggtag cggtggtttt tttgtttgca agcagcagat tacgcgcaga aaaaaggat   11460 ctcaagaaga tcctttgatc ttttctacgg gtctgacgc tcagtggaac gaaaactcac   11520
gttaagggat tttggtcatg catgatatat ctcccaattt gtgtagggct tattatgcac   11580
gcttaaaaat aataaagca gacttgacct gatagtttgg ctgtgagcaa ttatgtgctt   11640
agtgcatcta atcgcttgag ttaacgccgg cgaagcggcg tcggcttgaa cgaatttcta   11700
```

```
gctagacatt atttgccgac taccttggtg atctcgcctt tcacgtagtg gacaaattct    11760
tccaactgat ctgcgcgcga ggccaagcga tcttcttctt gtccaagata agcctgtcta    11820
gcttcaagta tgacgggctg atactgggcc ggcaggcgct ccattgccca gtcggcagcg    11880
acatccttcg gcgcgatttt gccggttact gcgctgtacc aaatgcggga caacgtaagc    11940
actacatttc gctcatcgcc agcccagtcg ggcggcgagt tccatagcgt taaggtttca    12000
tttagcgcct caaatagatc ctgttcagga accggatcaa agagttcctc cgccgctgga    12060
cctaccaagg caacgctatg ttctcttgct tttgtcagca agatagccag atcaatgtcg    12120
atcgtggctg gctcgaagat acctgcaaga atgtcattgc gctgccattc tccaaattgc    12180
agttcgcgct tagctggata acgccacgga atgatgtcgt cgtgcacaac aatggtgact    12240
tctacagcgc ggagaatctc gctctctcca ggggaagccg aagtttccaa aaggtcgttg    12300
atcaaagctc gccgcgttgt ttcatcaagc cttacggtca ccgtaaccag caaatcaata    12360
tcactgtgtg gcttcaggcc gccatccact gcggagccgt acaaatgtac ggccagcaac    12420
gtcggttcga gatggcgctc gatgacgcca actacctctg atagttgagt cgatacttcg    12480
gcgatcaccg cttcccccat gatgtttaac tttgttttag ggcgactgcc ctgctgcgta    12540
acatcgttgc tgctccataa catcaaacat cgacccacgg cgtaacgcgc ttgctgcttg    12600
gatgcccgag gcatagactg taccccaaaa aaacatgtca taacaagaag ccatgaaaac    12660
cgccactgcg ccgttaccac cgctgcgttc ggtcaaggtt ctggaccagt tgcgtgacgg    12720
cagttacgct acttgcatta cagcttacga accgaacgag gcttatgtcc actgggttcg    12780
tgcccgaat                                                            12789

<210> SEQ ID NO 10
<211> LENGTH: 20
<212> TYPE: DNA
<213> ORGANISM: Artificial Sequence
<220> FEATURE:
<223> OTHER INFORMATION: degenerate primer ALGG39
<220> FEATURE:
<221> NAME/KEY: misc_feature
<222> LOCATION: (3)..(3)
<223> OTHER INFORMATION: Inosine
<220> FEATURE:
<221> NAME/KEY: misc_feature
<222> LOCATION: (9)..(9)
<223> OTHER INFORMATION: Inosine
<220> FEATURE:
<221> NAME/KEY: misc_feature
<222> LOCATION: (11)..(11)
<223> OTHER INFORMATION: Inosine
<220> FEATURE:
<221> NAME/KEY: misc_feature
<222> LOCATION: (15)..(15)
<223> OTHER INFORMATION: g or a
<220> FEATURE:
<221> NAME/KEY: misc_feature
<222> LOCATION: (18)..(18)
<223> OTHER INFORMATION: any base

<400> SEQUENCE: 10
ccargykcag gaaaracnac                                                    20

<210> SEQ ID NO 11
<211> LENGTH: 20
<212> TYPE: DNA
<213> ORGANISM: Artificial Sequence
<220> FEATURE:
<223> OTHER INFORMATION: degenerate primer ALGG40
<220> FEATURE:
<221> NAME/KEY: misc_feature
```

```
<222> LOCATION: (3)..(3)
<223> OTHER INFORMATION: Inosine
<220> FEATURE:
<221> NAME/KEY: misc_feature
<222> LOCATION: (15)..(15)
<223> OTHER INFORMATION: any base
<220> FEATURE:
<221> NAME/KEY: misc_feature
<222> LOCATION: (18)..(18)
<223> OTHER INFORMATION: any base

<400> SEQUENCE: 11
acackyttyt tytgnccncc                                          20

<210> SEQ ID NO 12
<211> LENGTH: 8
<212> TYPE: DNA
<213> ORGANISM: Artificial Sequence
<220> FEATURE:
<223> OTHER INFORMATION: degenerate primer ALGG41
<220> FEATURE:
<221> NAME/KEY: misc_feature
<222> LOCATION: (6)..(6)
<223> OTHER INFORMATION: any base
<220> FEATURE:
<221> NAME/KEY: misc_feature
<222> LOCATION: (5)..(5)
<223> OTHER INFORMATION: g or a
<220> FEATURE:
<221> NAME/KEY: misc_feature
<222> LOCATION: (3)..(3)
<223> OTHER INFORMATION: any base

<400> SEQUENCE: 12 tcnarncc                                                        8

<210> SEQ ID NO 13
<211> LENGTH: 23
<212> TYPE: DNA
<213> ORGANISM: Artificial Sequence
<220> FEATURE:
<223> OTHER INFORMATION: degenerate primer ALGG42
<220> FEATURE:
<221> NAME/KEY: misc_feature
<222> LOCATION: (3)..(3)
<223> OTHER INFORMATION: Inosine
<220> FEATURE:
<221> NAME/KEY: misc_feature
<222> LOCATION: (6)..(6)
<223> OTHER INFORMATION: Inosine
<220> FEATURE:
<221> NAME/KEY: misc_feature
<222> LOCATION: (9)..(9)
<223> OTHER INFORMATION: Inosine
<220> FEATURE:
<221> NAME/KEY: misc_feature
<222> LOCATION: (12)..(12)
<223> OTHER INFORMATION: Inosine
<220> FEATURE:
<221> NAME/KEY: misc_feature
<222> LOCATION: (15)..(15)
<223> OTHER INFORMATION: any base
<220> FEATURE:
<221> NAME/KEY: misc_feature
<222> LOCATION: (18)..(18)
<223> OTHER INFORMATION: any base

<400> SEQUENCE: 13
ggagtaytaa cagcnytnat ggg                                      23

<210> SEQ ID NO 14
<211> LENGTH: 23
<212> TYPE: DNA
```

```
-continued

<213> ORGANISM: Artificial Sequence
<220> FEATURE:
<223> OTHER INFORMATION: degenerate primer ALGG43
<220> FEATURE:
<221> NAME/KEY: misc_feature
<222> LOCATION: (3)..(3)
<223> OTHER INFORMATION: any base
<220> FEATURE:
<221> NAME/KEY: misc_feature
<222> LOCATION: (18)..(18)
<223> OTHER INFORMATION: any base
<220> FEATURE:
<221> NAME/KEY: misc_feature
<222> LOCATION: (5)..(5)
<223> OTHER INFORMATION: g or a
<220> FEATURE:
<221> NAME/KEY: misc_feature
<222> LOCATION: (21)..(21)
<223> OTHER INFORMATION: g or a
<220> FEATURE:
<221> NAME/KEY: misc_feature
<222> LOCATION: (12)..(12)
<223> OTHER INFORMATION: Inosine
<220> FEATURE:
<221> NAME/KEY: misc_feature
<222> LOCATION: (15)..(15)
<223> OTHER INFORMATION: Inosine

<400> SEQUENCE: 14
tcnarcatcc aagtagcngg rtt                                          23

<210> SEQ ID NO 15
<211> LENGTH: 8
<212> TYPE: DNA
<213> ORGANISM: Artificial Sequence
<220> FEATURE:
<223> OTHER INFORMATION: degenerate primer ALGG44
<220> FEATURE:
<221> NAME/KEY: misc_feature
<222> LOCATION: (6)..(6)
<223> OTHER INFORMATION: g or a

<400> SEQUENCE: 15 ckccarta                                                            8
```

US 7,622,634 B2

USE OF GENES ENCODING MEMBRANE TRANSPORTER PUMPS TO STIMULATE THE PRODUCTION OF SECONDARY METABOLITES IN BIOLOGICAL CELLS

CROSS-REFERENCE TO RELATED APPLICATION

This application is a continuation of PCT International Patent Application No. PCT/EP/02/04322, filed on Apr. 18, 2002, designating the United States of America, and published, in English, as PCT International Publication No. WO 02/083888 A2 on Oct. 24, 2002, the contents of the entirety of which is incorporated by this reference.

TECHNICAL FIELD

The invention relates generally to biotechnology, and more specifically to the field of secondary metabolite production in plants and plant cell cultures. Particularly, the invention relates to the use of transporters and more particularly ABC-transporters to enhance the production and/or secretion of secondary metabolites in plants and plant cell cultures.

BACKGROUND

Higher plants are able to produce a large number of small-molecular-weight compounds with very complex structures. These compounds, called "secondary metabolites", can play a role in the resistance against pests and diseases, attraction of pollinators and interaction with symbiotic microorganisms. Besides the importance for the plant itself, secondary metabolites are of great commercial interest because they determine the quality of food (color, taste, and aroma) and ornamental plants (flower color, smell). A number of secondary metabolites isolated from plants are commercially available as fine chemicals, for example, drugs, dyes, flavours, fragrances and even pesticides. In addition, various health improving effects and disease preventing activities of secondary metabolites have been discovered, such as anti-oxidative and anti-metastatic-lowering properties (e.g., vinblastine, taxol).

Although about 100,000 plant secondary metabolites are already known, only a small percentage of all plants have been studied to the extent necessary for the determination of the presence of secondary metabolites. It is expected that interest in such metabolites will continue to grow as for example, plant sources of new and useful drugs are discovered. Some of these valuable phytochemicals are quite expensive because they are only produced at extremely low levels in plants.

Very little is known about the biosynthesis of secondary metabolites in plants. However, some recently elucidated biosynthetic pathways of secondary metabolites are long and complicated requiring multiple enzymatic steps to produce the desired end product. Most often, the alternative of producing these secondary metabolites through chemical synthesis is complicated due to a large number of asymmetric carbons and in most cases chemical synthesis is not economically feasible.

The recovery of valuable secondary metabolites is mostly achieved through extraction and purification (generally at low yields) of imported, sometimes exotic, plant biomasses, whose reproductive agriculture and secure long term supply are often very difficult, if not impossible to guarantee. The problems of obtaining useful metabolites from natural sources may potentially be circumvented by cell culture. The culture of plant cells has been explored since the 1960's as a viable alternative for the production of complex phytochemicals of industrial interest. Although plant cell cultures might be somewhat sensitive for shear forces, many cultures can be grown in large bioreactors without difficulty. For example, the use of large-scale plant cell cultures in bioreactors for the production of alkaloids has been extensively studied (Verpoorte et al. (1999) *Biotechnol. Lett.* 21, 467). Since it has been observed that undifferentiated cultures such as callus and cell suspension cultures produce only very low levels of secondary metabolites one tends to use differentiated plant cell cultures such as root- and hairy root-culture. For example, tropane alkaloids that are only scarcely synthesized in undifferentiated cells are produced at relatively high levels in cultured roots.

Despite the promising features and developments, the production of plant-derived pharmaceuticals by plant cell cultures has not been fully commercially exploited. The main reasons for this reluctance shown by industry to produce secondary metabolites by means of cell cultures, compared to the conventional extraction of whole plant material, are economical ones based on the slow growth and the low production levels of secondary metabolites by such plant cell cultures. Important causes are the toxicity of such compounds to the plant cell, and the role of catabolism of the secondary metabolites. Another important problem is that secondary metabolites are mostly retained intracellularly complicating the downstream processing and purification. Indeed, often laborious extraction schemes have to be developed for each specific secondary metabolite of interest.

DISCLOSURE OF THE INVENTION

The invention provides a solution to these problems. The invention uses genes encoding ABC-transporters to enhance the production of secondary metabolites in plant cell cultures. ABC-transporters are well-known in the field of cancer therapy as molecular 'pumps' in tumour-cell membranes that actively expel chemotherapy drugs from the interior of the cells. This allows tumour cells to avoid the toxic effects of the drug or molecular processes within the nucleus or the cytoplasm.

The two pumps commonly found to confer chemoresistance in cancer are P-glycoprotein and the so-called multidrug resistance-associated protein (MRP). In addition, ABC-transporters have been used in plants as a selection marker (PCT International Patent Publication WO 99/10514) and for the protection of plants for the detrimental effects of certain exogenously added xenobiotics (PCT International Patent Publication No. WO 00/18886, Muhitch J. M. et al. (2000) *Plant Science,* 157, 201). In U.S. Pat. No. 6,166,290, it is shown that the use of ABC-transporters in plants can be used to stimulate remediation, to strengthen the disease response and to modulate plant pigmentation. It has, however, never been shown in the art that ABC-transporters can be used to enhance the level of secondary metabolites made in plant cell cultures neither has it been shown that ABC-transporters can be used to stimulate the secretion of endogenously synthesized secondary metabolites from the inside of plant cells to the extracellular space.

DETAILED DESCRIPTION OF THE INVENTION

Figure 1:
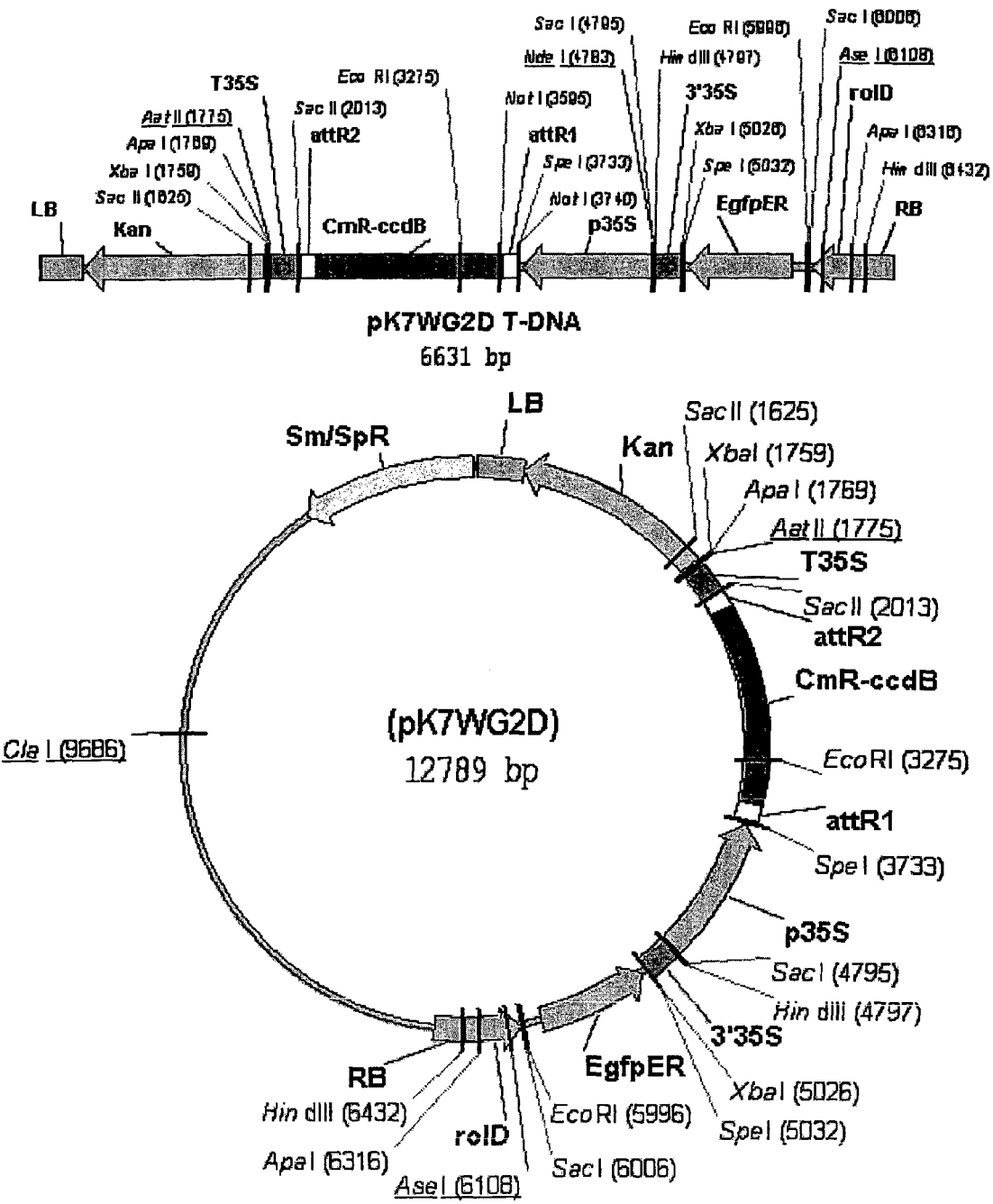
FIG. 1: Plasmid map of the pK7WGD2 binary vector.

The present invention accordingly provides in one embodiment a method for inducing or enhancing the production or the secretion of at least one secondary metabolite in biological cells by transformation of the biological cells with an expression vector comprising an expression cassette that further comprises a gene coding for a transporter. With "at least one secondary metabolite" it is meant related structures of secondary metabolites and intermediates or precursors thereof. The biological cells can be plant cells, fungal cells, bacteria cells, algae cells and/or animal cells. A "transporter" is a protein capable of interacting with at least one specific secondary metabolite and transporting the metabolite across a membrane wherein the membrane comprises the vacuolar membrane (tonoplast), or chloroplast membrane or plasma membrane. The transporter gene can be heterologous or homologous to the biological cell.

"Expression cassettes", of the present invention are generally DNA constructs preferably including (5' to 3' in the direction of transcription): a promoter region, a gene encoding for a transporter operatively linked with the transcription initiation region, and a termination sequence including a stop signal for RNA polymerase and a polyadenylation signal. It is understood that all of these regions should be capable of operating in the biological cells to be transformed. The promoter region comprising the transcription initiation region, which preferably includes the RNA polymerase binding site, and the polyadenylation signal may be native to the biological cell to be transformed or may be derived from an alternative source, where the region is functional in the biological cell.

The transporters of this invention may be expressed in for example a plant cell under the control of a promoter that directs constitutive expression or regulated expression. Regulated expression comprises temporally or spatially regulated expression and any other form of inducible or repressible expression. "Temporally" means that the expression is induced at a certain time point, for instance, when a certain growth rate of the plant cell culture is obtained (e.g., the promoter is induced only in the stationary phase or at a certain stage of development).

"Spatially" means that the promoter is only active in specific organs, tissues, or cells (e.g., only in roots, leaves, epidermis, guard cells or the like. Other examples of regulated expression comprise promoters whose activity is induced or repressed by adding chemical or physical stimuli to the plant cell. In a preferred embodiment, the expression of the transporters is under control of environmental, hormonal, chemical, and/or developmental signals, also can be used for expression of transporters in plant cells, including promoters regulated by (1) heat, (2) light, (3) hormones, such as abscisic acid and methyl jasmonate (4) wounding or (5) chemicals such as salicylic acid, chitosans or metals. Indeed, it is well known that the expression of secondary metabolites can be boosted by the addition of for example specific chemicals, jasmonate and elicitors. The co-expression of transporters, in combination with a stimulation of secondary metabolite synthesis is beneficial for an optimal and enhanced production of secondary metabolites. Alternatively, the transporters can be placed under the control of a constitutive promoter. A constitutive promoter directs expression in a wide range of cells under a wide range of conditions. Examples of constitutive plant promoters useful for expressing heterologous polypeptides in plant cells include, but are not limited to, the cauliflower mosaic virus (CaMV) 35S promoter, which confers constitutive, high-level expression in most plant tissues including monocots; the nopaline synthase promoter and the octopine synthase promoter.

The expression cassette is usually provided in a DNA or RNA construct which is typically called an "expression vector" which is any genetic element, for example, a plasmid, a chromosome, a virus, behaving either as an autonomous unit of polynucleotide replication within a cell (i.e., capable of replication under its own control) or being rendered capable of replication by insertion into a host cell chromosome, having attached to it another polynucleotide segment, so as to bring about the replication and/or expression of the attached segment. Suitable vectors include, but are not limited to, plasmids, bacteriophages, cosmids, plant viruses and artificial chromosomes. The expression cassette may be provided in a DNA construct which also has at least one replication system. In addition to the replication system, there will frequently be at least one marker present, which may be useful in one or more hosts or different markers for individual hosts. The markers may a) code for protection against a biocide, such as antibiotics, toxins, heavy metals, certain sugars or the like; b) provide complementation, by imparting prototrophy to an auxotrophic host: or c) provide a visible phenotype through the production of a novel compound in the plant.

Exemplary genes which may be employed include neomycin phosphotransferase (NPTII), hygromycin phosphotransferase (HPT), chloramphenicol acetyltransferase (CAT), nitrilase, and the gentamycin resistance gene. For plant host selection, non-limiting examples of suitable markers are β-glucuronidase, providing indigo production, luciferase, providing visible light production, Green Fluorescent Protein and variants thereof, NPTII, providing kanamycin resistance or G418 resistance, HPT, providing hygromycin resistance, and the mutated aroA gene, providing glyphosate resistance.

The term "promoter activity" refers to the extent of transcription of a gene that is operably linked to the promoter whose promoter activity is being measured. The promoter activity may be measured directly by measuring the amount of RNA transcript produced, for example by Northern blot or indirectly by measuring the product coded for by the RNA transcript, such as when a reporter gene is linked to the promoter.

The term "operably linked" refers to linkage of a DNA segment to another DNA segment in such a way as to allow the segments to function in their intended manners. A DNA sequence encoding a gene product is operably linked to a regulatory sequence when it is ligated to the regulatory sequence, such as, for example a promoter, in a manner which allows modulation of transcription of the DNA sequence, directly or indirectly. For example, a DNA sequence is operably linked to a promoter when it is ligated to the promoter downstream with respect to the transcription initiation site of the promoter and allows transcription elongation to proceed through the DNA sequence. A DNA for a signal sequence is operably linked to DNA coding for a polypeptide if it is expressed as a pre-protein that participates in the transport of the polypeptide. Linkage of DNA sequences to regulatory sequences is typically accomplished by ligation at suitable restriction sites or adapters or linkers inserted in lieu thereof using restriction endonucleases known to one of skill in the art.

The term "heterologous DNA" or "heterologous RNA" refers to DNA or RNA that does not occur naturally as part of the genome or DNA or RNA sequence in which it is present, or that is found in a cell or location in the genome or DNA or RNA sequence that differs from that which is found in nature. Heterologous DNA and RNA (in contrast to homologous DNA and RNA) are not endogenous to the cell into which it is introduced, but has been obtained from another cell or synthetically or recombinantly produced. An example is a human gene, encoding a human protein, operably linked to a non-human promoter. Another example is a gene isolated from one plant species operably linked to a promoter isolated from another plant species. Generally, though not necessarily, such DNA encodes RNA and proteins that are not normally produced by the cell in which the DNA is transcribed or expressed. Similarly exogenous RNA encodes for proteins not normally expressed in the cell in which the exogenous RNA is present. Heterologous DNA or RNA may also refer to as foreign DNA or RNA. Any DNA or RNA that one of skill in the art would recognize as heterologous or foreign to the cell in which it is expressed is herein encompassed by the term heterologous DNA or heterologous RNA. Examples of heterologous DNA include, but are not limited to, DNA that encodes proteins, polypeptides, receptors, reporter genes, transcriptional and translational regulatory sequences, selectable or traceable marker proteins, such as a protein that confers drug resistance, RNA including mRNA and antisense RNA and ribozymes.

Generally, two basic types of metabolites are synthesized in cells, i.e. those referred to as primary metabolites and those referred to as secondary metabolites. A primary metabolite is any intermediate in, or product of the primary metabolism in cells. The primary metabolism in cells is the sum of metabolic activities that are common to most, if not all, living cells and are necessary for basal growth and maintenance of the cells. Primary metabolism thus includes pathways for generally modifying and synthesizing certain carbohydrates, proteins, fats and nucleic acids, with the compounds involved in the pathways being designated primary metabolites. In contrast hereto, secondary metabolites usually do not appear to participate directly in growth and development. They are a group of chemically very diverse products that often have a restricted taxonomic distribution. Secondary metabolites normally exist as members of closely related chemical families, usually of a molecular weight of less than 1500 Dalton, although some bacterial toxins are considerably longer. Secondary plant metabolites include, for example, alkaloid compounds (e.g., terpenoid indole alkaloids, tropane alkaloids, steroid alkaloids, polyhydroxy alkaloids), phenolic compounds (e.g., quinines, lignans and flavonoids), terpenoid compounds (e.g., monoterpenoids, iridoids, sesquiterpenoids, diterpenoids and triterpenoids). In addition, secondary metabolites include small molecules (i.e., those having a molecular weight of less than 600), such as substituted heterocyclic compounds which may be monocyclic or polycyclic, fused or bridged. Many plant secondary metabolites have value as pharmaceuticals. Plant pharmaceuticals include, for example, taxol, digoxin, colchicines, codeine, morphine, quinine, shikonin, ajmalicine, and vinblastine.

The definition of "alkaloids", of which more than 12,000 structures have been described already, includes all nitrogen-containing natural products which are not otherwise classified as peptides, non-protein amino acids, amines, cyanogenic glycosides, glucosinolates, cofactors, phytohormones or primary metabolites (such as purine and pyrimidine bases). The "calystegins" constitute a unique subgroup of the tropane alkaloid class (Goldmann et al. (1990) Phytochemistry, 29, 2125). They are characterized by the absence of an N-methyl substituent and a high degree of hydroxylation. TrIhydroxylated calystegins are summarized as the calystegin A-group, tetrahydroxylated calystegins as the B-group, and pentahydroxylated derivates form the C-group. Calystegins represent a novel structural class of polyhydroxy alkaloids possessing potent glycosidase inhibitory properties next to longer known classes of the monocyclic pyrrolidones (e.g., dihydroxymethyldihydroxy pyrrolidine) pyrrolines and piperidines (e.g., deoxynojirimycin), and the bicyclic pyrrolizidines (e.g., australine) and indolizidines (e.g., swainsonine and castanospermine). Glycosidase inhibitors are potentially useful as antidiabetic, antiviral, antimetastatic, and immunomodulatory agents.

In another embodiment, the invention provides a method for enhancing the production of at least one secondary metabolite in biological cells by transformation of the biological cells with an expression vector comprising an expression cassette further comprising a gene coding for an ABC transporter. Genes useful to be incorporated in an expression cassette for carrying out the present invention include those coding for ATP-binding cassette (ABC) transporters. Genes encoding ABC-transporters can be of any species or origin, including microorganisms, plant and animal (Higgins (1992) Ann. Rev. Cell Biol. 8, 67), but are preferably of plant or fungal origin. The ATP-binding cassette (ABC) transporters, also called the "traffic ATPases", comprise a superfamily of membrane proteins that mediate transport and channel functions in prokaryotes and eukaryotes (Higgins, C. F. (1992) Annu. Rev. Cell Biol. 8:67-113; Theodoulou F. (2000) Biochimica et Biophysica Acta 1465, 79). Typically, an ABC transporter contains two copies each of two structural units: a highly hydrophobic transmembrane domain (TMD), and a peripherally located ATP binding domain or nucleotide binding fold (NBF), which together are often necessary and sufficient to mediate transport. The TMD domains form the pathway via which the substrate crosses the membrane, and in some cases, have been shown to contribute to the substrate specificity. The NBFs are oriented towards the cytoplasmic side of the membrane and couple ATP hydrolysis to transport. Within the NBF is a conserved region of approximately 200 amino acids, consisting of the Walker A and B boxes separated by the ABC signature motif. It is this signature motif which distinguishes ABC transporters from other NTP binding proteins, such as the kinases, which also contain the Walker sequences. Sequence homology over the whole gene can be negligible between different ABC transporters, but in the conserved areas of the NBF it is typically 30-40% between family members, and this has proved useful in the isolation of ABC genes by approaches such as PCR and hybridization with degenerate nucleotides (Dudler R. et al (1998) Methods Enzymol. 292, 162). A great variety of specific substrates is transported by members of this family of transport proteins, including drugs, anorganic ions, amino acids, proteins, sugars, and polysaccharides. Eukaryotic ABC proteins include: P-glycoproteins, also known as multidrug resistance (MDR) proteins, which are associated with resistance to a wide range of hydrophobic drugs (MDR1; Gottesman, M. M. & Pastan, I. (1993) Annu. Rev. Biochem. 62:385-

427) or with phosphatidyl choline transport (MDR2; Ruetz, S. & Gros, P. (1994) Cell 77:1071-1081); CFTR, the cystic fibrosis transmembrane conductance regulator (Welsh, M. J. & Smith, A. E. (1993) Cell 73:1251-1254); TAP proteins, the transporters associated with antigen processing in mammalian cells (Androlewicz, M. J. et al 1994) Proc. Natl. Acad. Sci. USA 91:12716-12720); cMOAT/cMRP1, which is associated with transport of glutathione, glucuronide, and sulfate conjugates across the canalicular membrane (Buchler, M. et al. (1996) J. Biol. Chem. 271:15091-15098); and STE6, which exports the a-factor mating pheromone of *S. cerevisiae* (Michaelis, S. (1993) Semin. Cell Biol. 4:17-27) and PDR5, the pleiotropic drug resistance protein of yeast. Prokaryotic ABC proteins include periplasmic nutrient permeases, such as those responsible for uptake of maltose (MalFGK) and histidine (HisMPQ) in gram-negative bacteria, and toxin exporters such as those required for export of hemolysin (HlyB) and colicin (ColV) from *E. coli*. Sequence comparisons between MRP1 and other ABC transporters reveal two major subgroups among these proteins (Szczypka et al. (1994) J. Biol. Chem. 269, 22853). One subgroup comprises MRP1, the *Saccharomyces cerevisiae* cadmium factor (YCF1) gene, the Leishmania P-glycoprotein-related molecule (Lei/PgpA) and the CFTRs. The other subgroup comprises the multiple drug resistance proteins (MDRs), MHC transporters and STE6. Homologues of ABC-transporters have been identified in plant species. In *Arabidopsis thaliana*, the glutathione-conjugate transporter (MRP) is located in the vacuolar membrane and is responsible for sequestration of xenobiotics in the central vacuole. An MDR-like gene (at-pgp1) has also been identified in *A. thaliana*, which encodes a putative P-glycoprotein homolog. This atpgp1 gene was found to share significant sequence homology and structural organization with human MDR genes. Other MDR homologues have been found in potato and barley. Genes encoding ABC-transporters of the present invention which may be operably linked with a promoter for expression in a plant species may be derived from a chromosomal gene, cDNA, a synthetic gene, or combinations thereof.

In another embodiment, DNA sequences encoding ABC-transporters are used to enhance the production of at least one secondary metabolite in plant cells comprising the transformation of the plant cells with an expression vector comprising an expression cassette further comprising a gene coding for an ABC-transporter.

By the term "enhanced production" it is meant that the level of one or more metabolites may be enhanced by at least 20%, 30%, 40%, 50%, 60%, 70%, 80%, 90% or at least 100% relative to the untransformed plant cell which was used to transform with an expression vector comprising an expression cassette further comprising a gene coding for a transporter or an ABC-transporter. An enhanced production of a secondary metabolite can result in a detection of a higher level of secondary metabolites in the extracellular medium of the plant cell culture. Alternatively, a higher level of secondary metabolites can be detected inside the plant cells, for example in the vacuole.

The present invention can be practiced with any plant variety for which cells of the plant can be transformed with an expression cassette of the current invention and for which transformed cells can be cultured in vitro. Suspension culture, callus culture, hairy root culture, shoot culture or other conventional plant cell culture methods may be used (as described in: Drugs of Natural Origin, G. Samuelsson, 1999, ISBN 9186274813).

By "plant cells" it is understood any cell which is derived from a plant and can be subsequently propagated as callus, plant cells in suspension, organized tissue and organs (e.g., hairy roots).

Tissue cultures derived from the plant tissue of interest can be established. Methods for establishing and maintaining plant tissue cultures are well known in the art (see, e.g., Trigiano R. N. and Gray D. J. (1999), "Plant Tissue Culture Concepts and Laboratory Exercises", ISBN: 0-8493-2029-1; Herman E. B. (2000), "Regeneration and Micropropagation: Techniques, Systems and Media 1997-1999", Agricell Report). Typically, the plant material is surface-sterilized prior to introducing it to the culture medium. Any conventional sterilization technique, such as chlorinated bleach treatment can be used. In addition, antimicrobial agents may be included in the growth medium. Under appropriate conditions plant tissue cells form callus tissue, which may be grown either as solid tissue on solidified medium or as a cell suspension in a liquid medium.

A number of suitable culture media for callus induction and subsequent growth on aqueous or solidified media are known. Exemplary media include standard growth media, many of which are commercially available (e.g., Sigma Chemical Co., St. Louis, Mo.). Examples include Schenk-Hildebrandt (SH) medium, Linsmaier-Skoog (LS) medium, Murashige and Skoog (MS) medium, Gamborg's B5 medium, Nitsch & Nitsch medium, White's medium, and other variations and supplements well known to those of skill in the art (see, e.g., Plant Cell Culture, Dixon, ed. IRL Press, Ltd. Oxford (1985) and George et al., Plant Culture Media, Vol. 1, Formulations and Uses Exegetics Ltd. Wilts, UK, (1987)). For the growth of conifer cells, particularly suitable media include ½ MS, ½ L.P., DCR, Woody Plant Medium (WPM), Gamborg's B5 and its modifications, DV (Durzan and Ventimiglia, In Vitro Cell Dev. Biol. 30:219-227 (1994)), SH, and White's medium.

When secondary metabolites are produced in plant cell culture systems they usually have to be extracted and purified from the isolated plant cell mass which is an expensive process. It is known that plants can be made by means of genetic manipulation to store proteins in seed endosperm, from where they can be more easily extracted. It has also been described that some plant cells can secrete secondary metabolites can be secreted and that the secretion can be enhanced by for example the addition of elicitors (Kneer et al. (1999) J. Exp. Bot. 50, 1553) or by the addition of specific chemicals (Lee et al. (1998) Phytochemistry 49, 2342). It has however never been described that the secretion of secondary metabolites by plant cells can be induced or enhanced by the transformation of at least one specific gene into a plant cell. The present invention provides a solution for this problem by transformation of plant cells, producing secondary metabolites, with an expression cassette comprising a gene encoding an ABC-transporter. Therefore, in another embodiment of the invention, a DNA sequence encoding an ABC-transporter can be used to induce or enhance the secretion of at least one secondary metabolite produced in plant cell cultures comprising transforming the plant cells that are producing secondary metabolites, with an expression vector comprising an expression cassette further comprising a gene coding for an ABC-transporter, and selecting transformed plant cells with an induced or enhanced secretion of at least one secondary metabolite. Such transformed plant cells can be subsequently propagated using methods described herein before.

An "enhanced secretion of at least one secondary metabolite" means that there exists already a detectable secretion of the secondary metabolite(s) in the extracellular medium of the plant cell culture and that an increase of the secondary metabolite(s) can be measured by at least 20%, 30%, 40%, 50%, 60%, 70%, 80%, 90% or more than 90% compared to basal secretion by the untransformed plant cell culture. An "enhanced secretion" does not necessarily mean that there is a higher production, it can also mean that there is exists the same level of production but that the secretion is enhanced.

An "induced secretion of at least one secondary metabolite" means that there is no detectable secretion of the secondary metabolite(s) in the extracellular medium of the untransformed plant cell culture but that the detection becomes possible upon carrying out the transformation according to the invention.

Generally, secondary metabolites can be measured, intracellularly or in the extracellular space, by methods known in the art. Such methods comprise analysis by thin-layer chromatography, high pressure liquid chromatography, capillary chromatography, (gas chromatographic) mass spectrometric detection, radioimmunoassay (RIA) and enzyme immunoassay (ELISA).

In order to make clear what is meant by the word "secretion" in the current invention one has to make a clear distinction between the secretion of proteins which is mediated by an amino-terminal signal peptide and the secretion of secondary metabolites which is independent of an amino-terminal leader sequence. As the term is used herein, secretion means secretion of a secondary metabolite across the plasma membrane or secretion across both the plasma membrane and the cell wall of a plant cell. It should be noted that, in the scientific literature the term "secretion" often is used to indicated secretion into the apoplastic space, i.e. secretion across the plasma membrane but not across the cell wall.

In one aspect of the invention, there is no secretion of (a) secondary metabolite(s) into the growth medium. Then, the secretion can be induced by several possibilities: (1) by the transformation of the plant cell with a heterologous gene encoding an ABC-transporter or (2) by the overexpression of a homologous ABC-transporter which expressing is rate-limiting in the plant cell or (3) by the relocalization of a homologous or heterologous ABC-transporter from a vacuolar localization towards a membrane localization. In plants, proteins destined for the vacuole are sorted away from proteins destined for secretion at the trans-Golgi network, a process that requires the presence of positive sorting signals on the vacuolar proteins. Three types of sorting signals have been described for soluble vacuolar proteins in plants (Matsuoka and Neuhaus (1999) J. Exp. Botany 50, 165). Some proteins contain a cleavable amino-terminal propeptide that functions as a sorting signal while others contain a cleavable carboxy-terminal propeptide. Finally, a minor amount of plant proteins contains an internal vacuolar targeting determinant. According to the invention a homologous or heterologous ABC-transporter that is normally localized in the vacuolar membrane can be engineered by clipping off its vacuolar localization signal (carboxy-terminal or amino-terminal propeptide) or by deleting its internal vacuolar targeting determinant. If necessary a heterologous or homologous amino-terminal leader sequence is spliced to the gene encoding the homologous or heterologous ABC-transporter in order to provide entry into the secretion system. As a result the engineered ABC-transporter is not directed anymore in the secretion pathway towards its normal vacuolar localization but is deviated towards the extracellular space. However, due to the hydrophobic transmembrane signal present in ABC-transporters, the ABC-transporter is not secreted into the extracellular medium but remains sequestered into the plasma membrane of the plant cell. We show in the present invention that the novel intracellular localization of the ABC-transporter (from the vacuole to the plasma membrane) results in a secretion of the produced secondary metabolites into the medium of the plant cell culture.

In another aspect of the invention, there is already an existing, but low, level of secretion of (a) secondary metabolite(s) by the plant cell and then the secretion can be enhanced by (1) by the transformation of the plant cell with a heterologous gene encoding an ABC-transporter or (2) by the overexpression of a homologous ABC-transporter which expressing is rate-limiting in the plant cell or (3) by the relocalization of a homologous or heterologous ABC-transporter from a normal vacuolar localization towards a membrane localization.

In yet another aspect, an intermediary product of the secondary metabolite, which causes negative feedback inhibition on an enzymatic reaction step involved in the biosynthesis of the secondary metabolite, can be secreted by (1) by the transformation of the plant cell with a heterologous gene encoding an ABC-transporter or (2) by the overexpression of a homologous ABC-transporter which expressing is rate-limiting in the plant cell or (3) by the relocalization of a homologous or heterologous ABC-transporter from a vacuolar localization towards a membrane localization. The secretion of the intermediary product or an amount produced thereof reduces the negative feedback inhibition and consequently enhances the production of the secondary metabolite in the plant cell. The enhanced production of the secondary metabolite can be made secreted by the plant cell by the transformation of the already transformed plant cell, with a second expression cassette comprising a gene encoding an ABC transporter, according to the method described above. In this case of secretion, the directed secondary metabolites can be easily isolated from the surrounding medium since they are directed into the extracellular space. Consequently, the breaking up of the cells that is necessary in the case of intracellular production can be omitted.

In another embodiment, the production of secondary metabolites can be enhanced by stimulating the transport of secondary metabolites into the vacuole. In plants, the targeting of proteins and compounds into the vacuole is of particular interest (especially from the point of view of application) because the vacuole is the largest storage compartment in the cell for reserve substances, detoxification products and defense substances. The most important storage takes place in vacuoles in plant organs such as tubers, bulbs, roots and stems. Similar considerations also apply to substances that can be used in the control of pests or diseases, especially when those substances prove to be toxic to the plant itself. Indeed, in certain cases the vacuole also serves as a detoxification organelle by, for example, storing the detoxification products synthesized by the plant. According to the present invention secondary metabolites can also be made secreted into the vacuole (1) by the transformation of a plant cell with a heterologous gene encoding an ABC-transporter or (2) by the overexpression of a homologous ABC-transporter which expressing is rate-limiting in the plant cell or (3) by the relocalization of a homologous or heterologous ABC-transporter from a normally localized plasma membrane localization towards a vacuolar localization. To perform the relocalization it is necessary to modify the gene encoding an ABC-transporter by genetically fusing it to an amino-terminal or carboxy-terminal vacuolar localization signal or by the genetic modification through the introduction of an existing internal vacuolar localization signal. U.S. Pat. No. 6,054,637 provides detailed information of genetic modification of genes through the addition or clipping off plant vacuolar localization signals. We observe that the secretion or targeting of the produced secondary metabolites into the vacuole reduces the toxicity to the plant cell.

In yet another embodiment, an intermediary product of the secondary metabolite, which causes negative feedback inhibition on an enzymatic reaction step involved in the biosynthesis of the secondary metabolite, can be made sequestered into the vacuole by (1) the transformation of the plant cell with a heterologous gene encoding an ABC-transporter or by (2) the overexpression of a homologous ABC-transporter which expressing is rate-limiting in the plant cell or (3) by the relocalization of a homologous or heterologous ABC-transporter from a normal membrane localization towards a vacuolar localization. The import of the intermediary product, or an amount produced thereof, into the vacuole reduces the negative feedback inhibition of the enzymatic reaction which occurs outside the vacuole and consequently enhances the production of the secondary metabolite in the plant cell.

In another embodiment, the current invention can be combined with other known methods to enhance the production and/or the secretion of secondary metabolites in plant cell cultures such as (1) by improvement of the plant cell culture conditions, (2) by the transformation of the plant cells with a transcription factor capable of upregulating genes involved in the pathway of secondary metabolite formation, (3) by the addition of specific elicitors to the plant cell culture, and 4) by the induction of organogenesis.

In another embodiment of the invention, DNA sequences encoding ABC-transporters are used to enhance the production of at least one secondary metabolite in plants comprising the transformation of the plants with an expression vector comprising an expression cassette further comprising a gene coding for an ABC-transporter.

By the term "to enhance the production" it is meant that the level of one or more metabolites may be enhanced by at least 20%, 30%, 40%, 50%, 60%, 70%, 80%, 90% or at least 100% relative to the untransformed plant which was used to transform with an expression vector comprising an expression cassette further comprising a gene coding for a transporter or an ABC-transporter. An enhanced production of a secondary metabolite can result in a detection of a higher level of secondary metabolites in the plant, for example in the vacuole. In another embodiment, the enhanced production of at least one secondary metabolite leads to an enhanced secretion. In yet another embodiment, the same production of at least one secondary metabolite occurs in the transformed plant but an enhanced secretion of at least one secondary metabolite occurs by the transformed plant. Secondary metabolites can for example be efficiently produced by continuous secretion from the roots of hydroponically grown plants. This process of secretion is also been termed 'rhizosecretion'.

The term "plant" as used herein refers to vascular plants (e.g., gymnosperms and angiosperms). The method comprises transforming a plant cell with an expression cassette of the present invention and regenerating such plant cell into a transgenic plant. Such plants can be propagated vegetatively or reproductively. The transforming step may be carried out by any suitable means, including by *Agrobacterium*-mediated transformation and non-*Agrobacterium*-mediated transformation, as discussed in detail below. Plants can be regenerated from the transformed cell (or cells) by techniques known to those skilled in the art. Where chimeric plants are produced by the process, plants in which all cells are transformed may be regenerated from chimeric plants having transformed germ cells, as is known in the art. Methods that can be used to transform plant cells or tissue with expression vectors of the present invention include both *Agrobacterium* and non-*Agrobacterium* vectors. *Agrobacterium*-mediated gene transfer exploits the natural ability of *Agrobacterium tumefaciens* to transfer DNA into plant chromosomes and is described in detail in Gheysen, G., Angenon, G. and Van Montagu, M. 1998. *Agrobacterium*-mediated plant transformation: a scientifically intriguing story with significant applications. In K. Lindsey (Ed.), Transgenic Plant Research. Harwood Academic Publishers, Amsterdam, pp. 1-33 and in Stafford, H. A. (2000) Botanical Review 66: 99-118. A second group of transformation methods is the non-*Agrobacterium* mediated transformation and these methods are known as direct gene transfer methods. An overview is brought by Barcelo, P. and Lazzeri, P. A. (1998) Direct gene transfer: chemical, electrical and physical methods. In K. Lindsey (Ed.), Transgenic Plant Research, Harwood Academic Publishers, Amsterdam, pp.35-55. Hairy root cultures can be obtained by transformation with virulent strains of *Agrobacterium rhizogenes*, and they can produce high contents of secondary metabolites characteristic to the mother plant. Protocols used for establishing of hairy root cultures vary, as well as the susceptibility of plant species to infection by *Agrobacterium* (Toivunen L. (1993) Biotechnol. Prog. 9, 12; Vanhala L. et al. (1995) Plant Cell Rep. 14, 236). It is known that the *Agrobacterium* strain used for transformation has a great influence on root morphology and the degree of secondary metabolite accumulation in hairy root cultures. It is possible that by systematic clone selection e.g., via protoplasts, to find high yielding, stable, and from single cell derived-hairy root clones. This is possible because the hairy root cultures possess a great somaclonal variation. Another possibility of transformation is the use of viral vectors (Turpen TH (1999) *Philos Trans R Soc Lond B Biol Sci* 354(1383): 665-73).

Any plant tissue or plant cells capable of subsequent clonal propagation, whether by organogenesis or embryogenesis, may be transformed with an expression vector of the present invention. The term 'organogenesis' means a process by which shoots and roots are developed sequentially from meristematic centers; the term 'embryogenesis' means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include protoplasts, leaf disks, pollen, embryos, cotyledons, hypocotyls, megagametophytes, callus tissue, existing meristematic tissue (e.g., apical meristems, axillary buds, and root meristems), and induced meristem tissue (e.g., cotyledon meristem and hypocotyls meristem).

These plants may include, but are not limited to, plants or plant cells of agronomically important crops, such as tomato, tobacco, diverse herbs such as oregano, basilicum and mint. It may also be applied to plants that produce valuable compounds, e.g., useful as for instance pharmaceuticals, as ajmalicine, vinblastine, vincristine, ajmaline, reserpine, rescinnamine, camptothecine, ellipticine, quinine, and quinidien, taxol, morphine, scopolamine, atropine, cocaine, sanguinarine, codeine, genistein, daidzein, digoxin, colchicines, calystegins or as food additives such as anthocyanins, vanillin; including but not limited to the classes of compounds mentioned above. Examples of such plants include, but not limited to, *Papaver* spp., *Rauvolfia* spp., *Taxus* spp., *Cinchona* spp., *Eschscholtzia californica, Camptotheca acuminata, Hyoscyamus* spp., *Berberis* spp., *Coptis* spp., *Datura* spp., *Atropa* spp., *Thalictrum* spp., *Peganum* spp.

In another embodiment, the invention provides an isolated polypeptide selected from the groups consisting of (a) an isolated polypeptide encoded by a polynucleotide comprising the sequence of SEQ ID NO: 1 of the accompanying SEQUENCE LISTING, the contents of which are incorporated by this reference; (b) an isolated polypeptide comprising a polypeptide sequence having a least 83% identity to the polypeptide sequence of SEQ ID NO: 2; (c) fragments and variants of such polypeptides in (a) to (b) that induce or enhance the production or the secretion of at least one secondary metabolite in plants or plant cells.

In another embodiment, the invention provides an isolated polynucleotide selected from the groups consisting of (a) an isolated polynucleotide comprising a polynucleotide sequence of SEQ ID NO: 1; (b) an isolated polynucleotide comprising a polynucleotide sequence having at least 91% identity to SEQ ID NO: 1; (c) fragments and variants of such polynucleotides in (a) to (b) that induce or enhance the production or the secretion of at least one secondary metabolite in plants or plant cells.

As used herein, the words "polynucleotide" may be interpreted to mean the DNA and cDNA sequence as detailed by Yoshikai et al. (1990) Gene 87:257, with or without a promoter DNA sequence as described by Salbaum et al. (1988) *EMBO J* 7(9):2807.

As used herein, "fragment" refers to a polypeptide or polynucleotide of at least about 9 amino acids or 27 base pairs, typically 50 to 75, or more amino acids or base pairs, wherein the polypeptide contains an amino acid core sequence. If desired, the fragment may be fused at either terminus to additional amino acids or base pairs, which may number from 1 to 20, typically 50 to 100, but up to 250 to 500 or more. A "functional fragment" means a polypeptide fragment possessing the biological property of that induce or enhance the production or the secretion of at least one secondary metabolite in plants or plant cells. The terms 'identical' or percent 'identity' in the context of two or more nucleic acids or polypeptide sequences, refer to two or more sequences or subsequences that are the same or have a specified percentage of amino acid residues or nucleotides that are the same (i.e., 70% identity over a specified region), when compared and aligned for maximum correspondence over a comparison window, or designated region as measured using sequence comparison algorithms or by manual alignment and visual inspection. Preferably, the identity exists over a region that is at least about 25 amino acids or nucleotides in length, or more preferably over a region that is 50-100 amino acids or nucleotides or even more in length. Examples of useful algorithms are PILEUP (Higgins & Sharp, CABIOS 5:151 (1989), BLAST and BLAST 2.0 (Altschul et al. J. Mol. Biol. 215: 403 (1990). Software for performing BLAST analyses is publicly available through the National Center for Biotechnology Information (www/ncbi.nlm.nih.gov).

The invention is further explained with the aid of the following illustrative Examples:

EXAMPLES

The recombinant DNA and molecular cloning techniques applied in the below examples are all standard methods well known in the art and are, for example, described by Sambrook et al. *Molecular cloning: A laboratory manual* (Cold Spring Harbor Laboratory Press, 2d ed. 1989). Methods for yeast culture and manipulation applied in the below examples are all standard methods well known in the art and are described, for example, in Guthrie and Fink *Guide to yeast genetics and molecular biology*, (Academic Press, Inc., New York, N.Y. 1991). Methods for tobacco cell culture and manipulation applied in the below examples are methods described in or derived from methods described in Nagata et al. (1992) Int. Rev. Cytol. 132, 1.

Example 1

Identification of Yeast Multidrug Resistance Transporters Specific for Tropane (Tas) and Nicotine-type Alkaloids (NAs)

In the yeast *Saccharomyces cerevisiae*, a complex pleiotropic drug resistance (PDR) network of genes involved in multidrug resistance is composed of the transcriptional regulators Pdr1p and Pdr3p, which activate expression of the ATP-binding cassette (ABC) transporter-encoding genes PDR5, SNQ2, YOR1, as well as other not yet identified genes. To assess yeast sensitivity towards tropane alkaloids (Tas) and nicotine alkaloids (Nas) and identify yeast ABC transporters with specificity for TAs and NAs, we have screened isogenic yeast strains deleted of the ABC transporters YOR1, SNQ2, PDR5, PDR10, PDR11 or YCF1 for tolerance to the toxic compounds hyoscyamine, scopolamine and nicotine. The isogenic yeast strains derived from the US50-18C genotype were constructed and described in Decottignies et al. (*J. Biol. Chem.* (1998) 273, 12612). The yeast strains derived from the BY4741 genotype are obtained from the EUROSCARF collection (Frankfurt, Germany). All strains are listed in Table 1.

TABLE 1

| Yeast strains used | |
|---|---|
| Strain | Genotype |
| US50-18C | Mata pdr1-3 ura3 his1 |
| AD1 | US50-18C yor1::hisG |
| AD2 | US50-18C snq2::hisG |
| AD3 | US50-18C pdr5::hisG |
| AD4 | US50-18C pdr10::hisG |
| AD5 | US50-18C pdr11::hisG |
| BY4741 | Mata his3Δ1 leu2Δ0 met15Δ0 ura3Δ0 |
| Y02409 | BY4741 pdr5::kanMX4 |
| Y03951 | BY4741 snq2::kanMX4 |
| Y04069 | BY4741 ycf1::kanMX4 |
| Y05933 | BY4741 yor1::kanMX4 |

Alkaloid tolerance was assessed by controlling growth performance on rich medium (YPD) that contained different concentrations of TAs or NAs. To this end the different strains were grown to saturation (48 h) in liquid YPD. Cultures were diluted 10-, 100- and 1000-fold, and volumes of about 3 μl were dropped with a stainless steel replicator on YPD plates containing 2% Bacto Agar with the toxic compounds. Rich medium contains 1% yeast extract, 2% Bacto Peptone and 2% glucose. Filter-sterilized water solutions of hyoscyamine, scopolamine and nicotine were added after autoclaving. Growth was evaluated after two days incubation at 28° C. We observed that wild type yeast (i.e., not deleted for one of the ABC transporters) can tolerate hyoscyamine, scopolamine and nicotine to levels of 50 mM, 100 mM, and 15 mM respectively. Gradually increasing alkaloid levels in the medium caused growth retardation and was finally lethal. All isogenic strains except the pdr5 mutant strain showed identical alkaloid sensitivity. The above-mentioned alkaloid concentrations were lethal for the strain deleted for the PDR5 gene. This indicates that Pdr5p shows substrate specificity for TAs and NAs and is the only known ABC transporter involved in TA or NA transport in yeast cells. Previously other plant secondary metabolites such as indole alkaloids (e.g., vinblastine and vincristine), taxol and flavonoids were also shown to be substrates for Pdr5p mediated multidrug transport (Kolaczkowski et al. (1996) J. Biol. Chem. 271, 31543 and Kolaczkowski et al. (1998) Microb. Drug Resist. 4, 143).

Example 2

Assessment of Toxicity of Tas and Nas to Tobacco BY-2 Suspension Cultured Cells

Suspension cultured tobacco cells, Nicotiana tabacum L. cv BrightYellow 2 were grown in the dark at 26° C. on a rotary shaker (130 rpm) in MSST, a modified Murashige-Skoog basal medium supplemented with 1.5 mM $KH_2PO_4$, 3 µM thiamine, 0.55 mM inositol, 87 mM sucrose and 1 µM 2,4D. Cells are subcultured every 7 days by transferring 0.5 ml into 50 ml of fresh medium in 250-ml flasks.

Toxicity of TAs and NAs to tobacco BY-2 cells was assessed in two ways. In the first method growth performance on MSST medium containing different concentrations of TAs or NAs was controlled. To this end a fresh BY-2 cell culture was started and after 3 days culture volumes of about 300 µl were dropped on MSST plates containing 0.65% Bacto Agar and the toxic alkaloids. Filter-sterilized water solutions of hyoscyamine and nicotine were added after autoclaving. Growth was evaluated after 15 days incubation at 26° C. Wild type BY-2 cells (i.e., not transgenic) can tolerate hyoscyamine and nicotine without severe growth problems to levels of 30 mM and 3 mM respectively. A gradually increasing alkaloid level in the medium caused growth retardation and finally was lethal. In the second method toxicity was evaluated by measuring cell death after incubation in the presence of increasing levels of alkaloids. Cell death was scored by the Evans blue method (Turner and Novacky (1974) Phytopathol. 64, 885). To this end a fresh BY-2 cell culture was started and after 3 days 5 ml of this culture was transferred to one well of a 6-well plate (Falcon 353046). 1 ml of fresh MSST was added and the desired toxic compound in a volume of 650 µl in 0.1M potassium phosphate buffer at pH 5.8. Cells were then further incubated on the rotary shaker and 1-ml samples were taken after 0, 6 and 24 hours. We spun the cells down at 6000 rpm for 3 minutes, removed the supernatant, added 1 ml of 0.1% Evans blue in MSST medium and incubated for 15 minutes at room temperature on a rotary wheel. Afterwards we spun the cells down again and washed 5 times with fresh MSST medium till all the blue color was gone from the supernatant. Dye bound to dead cells was solubilized by incubation in 1 ml of 50% methanol, 1% SDS for 30 minutes at 50° C. We spun the cells down again (now at 14000 rpm for three minutes) and quantified cell death by measuring $OD_{600}$ of the supernatant. Cell death is expressed as fold increase in Evans blue staining compared to the control cells. In this assay tobacco BY-2 cells are found sensitive to all the compounds tested. Hyoscyamine and nicotine cause the death of all suspension cultured tobacco cells within 24 hours of incubation at levels of 50 mM and 20 mM respectively. This indicates that the metabolites that plants produce inside the cells can be toxic for themselves and also that this toxicity can result in slow growth of plant cells producing secondary metabolites. Furthermore these results provided us with useful assay systems fur evaluating the activity of ABC transporters from different organisms such as yeast, plants and animals in tobacco cell suspension cultures.

Example 3

Expression of PDR5 in Tobacco BY-2 Suspension Cultured Cells 3.1 Cloning of PDR5

The PDR5 gene was cloned by the PCR method with the PfuI polymerase. To this end oligonucleotides were designed with 5'-terminal attB sequences that amplify the entire open reading frame of the PDR5 gene (4536 nt) as a PCR product that is an efficient substrate for recombination with the Gateway™ system (Invitrogen). Gateway technology provides an alternative rapid method for cloning a sequence into a multiple expression system. The advantage of the Gateway cloning is that fragments present as Entry clones can be subcloned into different Destination vectors in a short time. This technology was used to construct a set of versatile vectors for Agrobacterium-based plant transformation. Our intention was to develop vectors for wide range plant gene analysis. The Gateway-compatible binary vector pPZP200 is the backbone of our constructs (Hajdukiewicz et al. Plant Molecular Biology 25, 989-994, 1994). This binary vector is relatively small in size, contains two origins of replication in E. coli or in Agrobacterium and posses streptomycin and/or spectinomycin for plasmid selection. Three plant selectable marker genes; kanamycin, hygromycin and bar (most frequently used markers in plant transformation) have been used for all constructs. All selectable markers are in a cassette containing nos (nopaline synthase) promoter and nos terminator. These genes were cloned toward the left border of the T-DNA. For construction of all Gateway clones we have used the rfA conversion cassette.

The oligonucleotides used for PDR5 gene cloning, are 5'-AAAAGCAGGCTACCATGCCCGAGGC-CAAGCTTAACAATA-3' (SEQ ID NO:3) as the forward primer and 5'-AGAAAGCTGGGTCCATCTTGG-TAAGTTTCTTTTCTTAACC-3' (SEQ ID NO:4) as the reverse primer, respectively. As a template, genomic DNA prepared from the yeast strains US50-18C or W303 was used. First the PCR fragments were introduced in the Donor Vector pDONR201 (Invitrogen) via the BP reaction to generate the Entry Clone. Then the PDR5 gene was transferred to the Destination Vector pK7WGD2 (FIG. 1) via the LR reaction, where the gene is under control of the CaMV 35S promoter. The T-DNA of the pK7WGD2 binary vector also bears the kanamycin resistance gene (NPTII) under the control of the pnos promoter as selectable marker for plant transformation and the gene encoding the green fluorescent protein (GFP) under the control of the prolD promoter for visual selection of transgenic plant cell lines. The resulting binary plasmids were designated pK7WGD2-ScPDR5-US50 or pK7WGD2-ScPDR5-W303 depending on the yeast genotype from which the gene is isolated. Also the GUS gene was introduced in the pK7WGD2 vector and the resulting binary vector pK7WGD2-GUS served as a control for the experiments described in the examples below.

3.2 Transformation of Tobacco BY-2 Suspension Cultured Cells

Plant cell transformations were carried out by applying the ternary vector system (van der Fits et al. (2000) Plant Mol. Biol. 43, 495). The plasmid pBBR1MCS-5.virGN54D is used as a ternary vector. The binary plasmid was introduced into Agrobacterium tumefaciens strain LBA4404 already bearing the ternary plasmid by electro-transformation.

Agrobacterium tumefaciens strains were grown for three days at 28° C. on solid LC medium containing 20 µg/ml rifampicin, 40 µg/ml geneticin, 100 µg/ml spectinomycin and 300 µg/ml streptomycin. LC medium contains 1% Bacto Trypton, 0.5% Bacto yeast extract and 0.8% NaCl. From these bacteria a 5-ml liquid culture was grown in LC medium for 48 hours. *N. tabacum* BY-2 cells were grown in MSST medium as described in example 2. For transformation 3 days old cell cultures were used. For cocultivation 4 ml of BY-2 cells was transferred to the corner of a Petri dish (Ø 80 mm) and 300 µl of the *A. tumefaciens* culture was added. Dishes were taped with respiratory tape and incubated for 3 days at 26° C. in the dark. After 3 days the cocultivation mixture was transferred into 20 ml of fresh MSST medium 50 µg/ml kanamycin-B, 500 µg/ml carbenicillin and 250 µg/ml vancomycin in 100-ml flasks and further incubated as described in example 2. After one week 4 ml of this cell suspension culture was subcultured in 40 ml of fresh MSST medium with 10 µg/ml of the kanamycin analogue G-418 (geneticin), 500 µg/ml carbenicilin and 250 µg/ml vancomycin and grown further till it reached maximal density (similar to stationary, 1-week-old culture) which took two to three weeks, depending on the efficiency of the transformation event. After two additional 1 ml transfer cycles in medium containing 50 µg/ml kanamycin-B, 500 µg/ml carbenicilin and 250 µg/ml vancomycin cells were further propagated in an antibiotic-free MSST medium as described in example 2. Elimination of agrobacteria was verified and efficient transgene expression was scored in vivo observing GFP fluorescence with a fluorescence microscope equipped with HQ-GFP band-pass filters for an excitation at 470 and emission at 525 nm.

Figure 2:
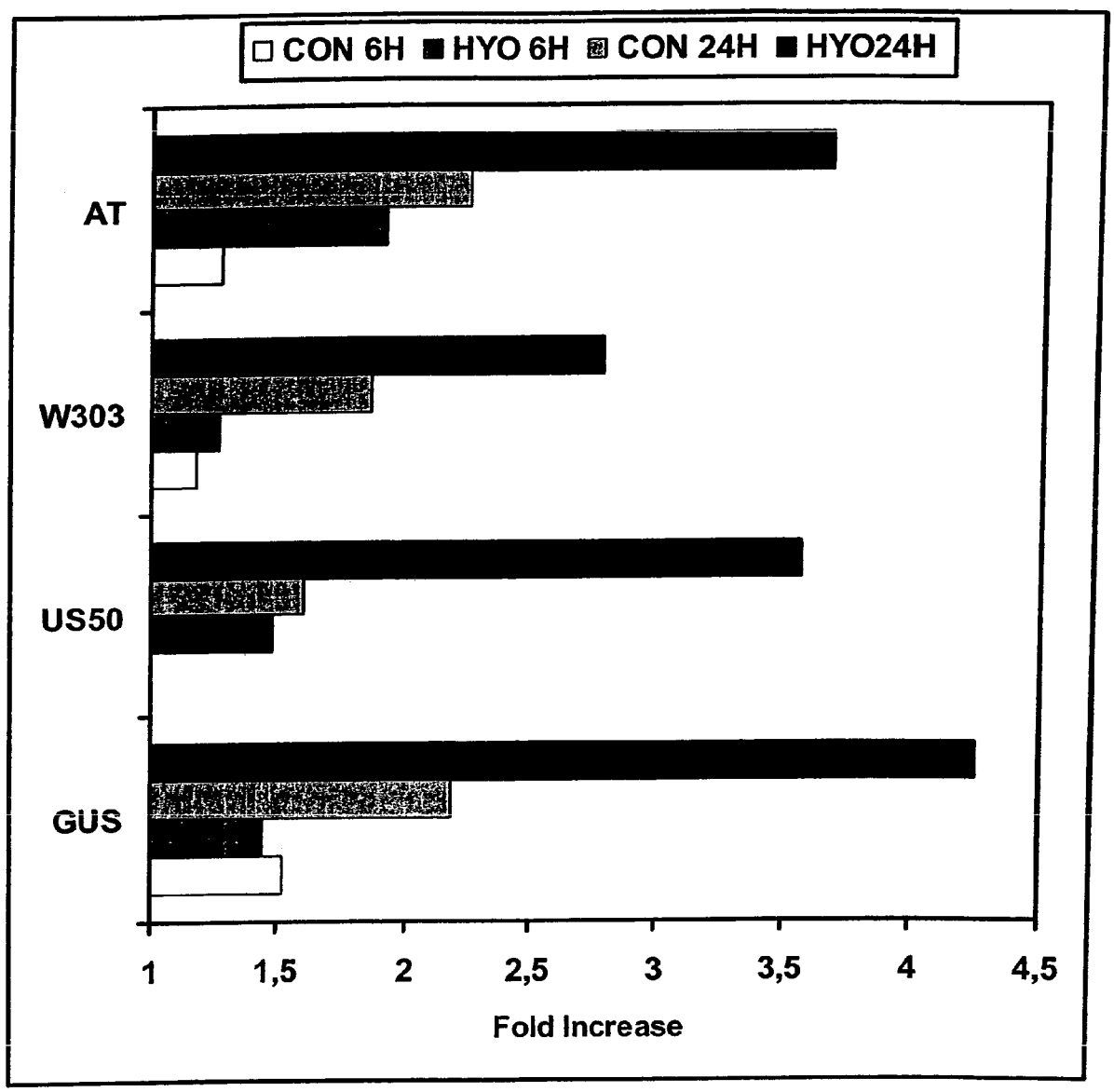
FIG. 2: Hyoscyamine-induced cell death in transformed BY-2 cells. Three-day old transformed BY-2 cell cultures were incubated in the absence (CON) or presence (HYO) of 30 mM hyoscyamine for 24 hours. Cell death was assayed at two time points (6 hours and 24 hours) by Evans blue staining and is indicated as the fold increase in optical density at $OD_{600}$ relative to the value at the start of the experiment. Values are the mean of three independent experiments. GUS, US50, W303 and AT represent BY-2 cell lines transformed with pK7WGD2-GUS, pK7WGD2-ScPDR5-US50, pK7WGD2-ScPDR5-W303 and pK7WGD2-AtPDR1 respectively.

3.3 Effect of Heterologous PDR5 Expression in BY-2 Suspension Cultured Cells on Alkaloid Tolerance In recombinant BY-2 cells transformed with the PDR5 expression cassettes (from both yeast genotypes), correct PDR5 expression is tested by northern blot analysis using a PDR5 specific DNA probe and by western blot analysis using a rabbit polyclonal anti-Pdr5p antibody (Decottignies et al. (1999) J. Biol. Chem. 274, 37139). In both lines PDR5 is efficiently expressed both on the RNA and protein level. Fractionation also shows that the Pdr5 protein is correctly targeted to the plasma membrane. Tolerance of the transformed BY-2 suspension cultures to hyoscyamine and nicotine was assessed by the two assays described in example 2. As can be deduced from the growth performance assay, BY-2 cell lines expressing the different yeast Pdr5 transporters displayed to varying extents an increased tolerance to both alkaloids as compared to the control GUS-expressing lines. Lines expressing the PDR5 transporter from yeast genotype W303 showed the highest alkaloid tolerance, in particular towards hyoscyamine. In the cell death experiment hyoscyamine was added to a final concentration of 30 mM. Transgene BY-2 cells expressing the Pdr5p from yeast strain W303 again showed the highest tolerance to this tropane alkaloid (FIG. 2). Fold increase in cell death lowered with ca. 35% in the W303 lines whereas US50 lines had a 15% decrease in hyoscyamine induced cell death.

3.4 Effect of Heterologous PDR5 Expression in BY-2 Suspension Cultured Cells on Nicotinic Alkaloid Production For the analysis of nicotinic alkaloid accumulation, 6-day old recombinant BY-2 cell cultures (BY-2 transformed with pK7WGD2-ScPDR5-US50 or pK7WGD2-ScPDR5-W303 or pK7WGD2-GUS) were washed and diluted ten-fold with fresh hormone free MSST medium. After a recuperation period of 12 hours, the cultures were treated with methyl jasmonate (MeJA). MeJA was dissolved in dimethyl sulfoxide (DMSO) and added to the culture medium at a final concentration of 50 µM. As a control, cells treated with an equivalent amount of DMSO were included. For alkaloid analysis, three replicate snake flasks with a volume of 20 ml were processed. After vacuum-filtering through Miracloth, cells and medium were separated from each other for intracellular and extracellular alkaloid analysis respectively. The filtered cell mass was transferred to a test tube, frozen and lyophilized (50 mbar, approx. 48 hours). Lyophilized cell samples were extracted for GC-MS analysis by a modified method described by Furuya et al. (1971, Phytochemistry, 10, 1529). Cells were weighed and 25 µg 5-α-cholestane was added as internal standard. The samples are made alkaline with ammonia (10% (v/v), 1 ml) and water (2 ml) is added. Alkaloids were extracted by vortexing with 2 ml of dichloromethane. After 30 minutes, the samples were centrifuged (2000 rpm, 10 min) and the lower organic layer was separated and transferred into glass vials. After evaporation to dryness 25 µl of dichloromethane was added and the samples were silylated with N-methyl-N-(trimethylsilyl)trifluoroacetamide (Pierce, Rockford, Md., US) for 20 min at 120° C. prior to GC-MS analysis. For alkaloid determination in the medium, 20 ml of the filtered medium was made alkaline with ammonia (10% v/v) to reach pH 9. Internal standards were added (5-α-cholestane and cotinine). Subsequently this solution was extracted twice with dichloromethane (1:1) and evaporated to dryness. The column was rinsed twice with 1 ml of dichloromethane and the extract was transferred into glass vials. We further proceeded as described above for the cell extract.

TABLE 2

| BY-2 Strain | Alkaloid accumulation in transformed BY-2 cells[a] | | | | |
|---|---|---|---|---|---|
| | Nicotine[b] | | Anatabine[b] | | |
| medium | Medium | Cells | Medium | Cells | % in |
| GUS | 0 | 2.00 | 0.18 | 157 | 0.1 |
| ScPDR5-US50 | 0 | 0.88 | 7.40 | 207 | 3.6 |
| ScPDR5-W303 | 0 | 2.03 | 5.12 | 74 | 6.9 |

[a]Measured 72 hours after elicitation with 50 µM methyl jasmonate. Results are the mean of three independent experiments
[b]Indicated in µg/flask, with 20-ml BY-2 culture per flask In jasmonate elicited BY-2 cells, the alkaloids detected after 72 hours are nicotine, anabasine, anatabine, and anatalline. No alkaloids are detected in DMSO-treated samples, neither in the cells nor in the medium. The results for nicotine and anatabine are shown in Table 2. Of all alkaloids that are produced by elicited BY-2 cells only anatabine is found in the medium. Although only trace amounts of anatabine can be detected extracellularly, comparison of anatabine levels in the different BY-2 cell lines after 72 hours of MeJA treatment clearly shows an enhancement of anatabine export in cell lines transformed with the PDR5 genes.

Example 4

Expression of Vacuole Targeted PDR5 in Tobacco BY-2 Suspension Cultured Cells 4.1 Construction and Cloning of Recombinant PDR5

To target the yeast PDR5 protein to plant vacuolar membranes, two strategies are followed. In the first, the N-terminal signal peptide and pro-peptide from sweet potato (MKAFTLALFLALSLYLLPNPAHSRFNPIRLPTTHEPA (SEQ ID NO:5), Matsuoka and Nakamura (1991) Proc. Natl. Acad. Sci. USA 88, 834) are fused at the N-terminus of the Pdr5 protein. The resulting recombinant open reading frame is designated ScNVacPDR5. In the second approach the C-terminal amino acids of the tobacco chitinase A (DLLGNGLLVDTM (SEQ ID NO:6), Neuhaus et al. (1991) Proc. Natl. Acad. Sci. USA 88, 10362) are added at the C-terminus of the Pdr5 protein. The resulting recombinant open reading frame is designated ScPDR5CVac. Both recombinant genes are put under the control of the CaMV35S promoter and cloned in the binary vector bearing the HYG and GFP genes as described in Example 3.1. The resulting binary plasmids are designated pH-ScNVacPDR5-GFP and pH-ScPDR5CVac-GFP, respectively.

4.2 Effect of Recombinant PDR5 Expression in BY-2 Suspension Cultured Cells on Alkaloid Tolerance and Nicotine Production BY-2 suspension cultured cells are transformed as described in Example 3.2 and 5 transgene calli of both ScNVacPDR5 or ScPDR5CVac transformed cells and highly expressing GFP are selected as described in Example 3.3. Control of expression of recombinant PDR5 is performed as described in Example 3.3 by northern and western blot analysis. Fractionation shows that in both types of transgene lines (NVac or CVac) the Pdr5 protein is targeted to the vacuolar membrane.

To assess tolerance to nicotine and hyoscyamine in transgenic cell lines the same assays as described in Example 3.3 are used here to evaluate the functionality of vacuole targeted Pdr5p. The effect of the vacuolar expression of PDR5 on nicotine production in BY-2 cells is evaluated as described in Example 3.4.

Example 5

Expression of Plant PDR Orthologues in Tobacco BY-2 Suspension Cultured Cells 5.1. Cloning of AtPDR1

The ABC protein super-family is the largest protein family known and most are membrane proteins active in the transport of a broad range of substances across the membranes. Also in *Arabidopsis* this superfamily is large and diverse (129 ORFs) and a complete inventory has been described by Sanchez-Fernandez et al. (J. Biol. Chem. (2001), 276, 30231). One of the subfamilies of full-length ABC transporters in *Arabidopsis* consists of the PDRs (13 ORFs) of which yeast PDR5 is the prototype. At least eight of the PDR5-like ORFs in *Arabidopsis* are transcriptionally active and have been isolated as ESTs (Sanchez-Fernandez et al. (2001), J. Biol. Chem., 276, 30231). Amongst these is one of the closest *Arabidopsis* PDR5-orthologues, namely the AtPDR1 gene (At3g16340). A cDNA clone of the AtPDR1 gene is isolated as described for the yeast PDR5 gene in Example 3.

To this end, the following oligonucleotides were designed: 5'-AAAAAGCAGGCTACCATGGAGACGT-TATCGAGAA-3' (SEQ ID NO:7) as the forward primer and 5'-AGAAAGCTGGGTCTATCGTTGTTG-GAAGTTGAGC-3' (SEQ ID NO:8) as the reverse primer, respectively. As a template we used cDNA prepared from *Arabidopsis hypocotyls*.

5.2 Cloning of HmPDR1

The biosynthesis of tropane alkaloids such as hyoscyamine and scopolamine in plants of the Solanaceae is very tissue-specific and occurs only in the roots. Later on, the alkaloids are transported to the aerial parts, especially the leaves, where they are finally accumulated. In hairy roots, however, this translocation cannot occur and part of the produced alkaloids is released in the medium. This release call be stimulated by the addition of millimolar amounts of $CdCl_2$ to the medium (Furze et al. (1991) Plant Cell Rep. 10, 111 and Pitta-Alvarez et al. (2000) Enzyme. Microb. Technol. 26, 252). This indicates the existence of active detoxifying mechanisms against cadmium in which also the tropane alkaloids would be involved. We applied this knowledge to isolate an alkaloid specific PDR-like gene from *Hyoscyamus muticus* hairy roots.

A cDNA clone of a PDR-like gene is isolated from *H. muticus* and is designated HmPDR1. To this end total RNA was prepared from hairy roots of the *H. muticus* KB7 line (Jouhikainen et al. (1999) Planta 208, 545) treated for 30 hours with 1 mM $CdCl_2$ and was reverse transcribed with the Superscript RTII reverse transcriptase. A nested PCR was subsequently carried out with the Taq DNA polymerase using the DNA-RNA hybrid as the template and two sets of degenerate primers designed from highly conserved amino acid sequences in the nucleotide binding folds of known yeast and plant PDR proteins (see, Table 3). This PCR yields two fragments derived from the two nucleotide-binding folds which are naturally present in the general tandem repeat structure of ABC proteins. Using specific primers and RT-PCR, 5'RACE and 3'RACE techniques we cloned a full-length cDNA clone, which is designated HmPDR1. The nucleotide sequence of the HmPDR1 cDNA clone is depicted in SEQ ID NO: 1, the amino acid sequence of the HmPDR1 protein is depicted in SEQ ID NO: 2.

TABLE 3

Degenerate primers used for HmPDR1 cDNA cloning

| Primer | Sequence | |
|---|---|---|
| ALGG39 | 5'-CCIRGYKCIGGIAARACNAC-3' | (SEQ ID NO:10) |
| ALGG40 | 5'-ACICKYTTYTTYTGNCCNCC-3' | (SEQ ID NO:11) |
| ALGG41 | 5'-TCNARNCC-3' | (SEQ ID NO:12) |
| ALGG42 | 5'-GGIGTIYTIACIGCNYTNATGGG-3' | (SEQ ID NO:13) |
| ALGG43 | 5'-TCNARCATCCAIGTIGCNGGRTT-3' | (SEQ ID NO:14) |
| ALGG44 | 5'-CKCCARTA-3' | (SEQ ID NO:15) |

Figure 3:
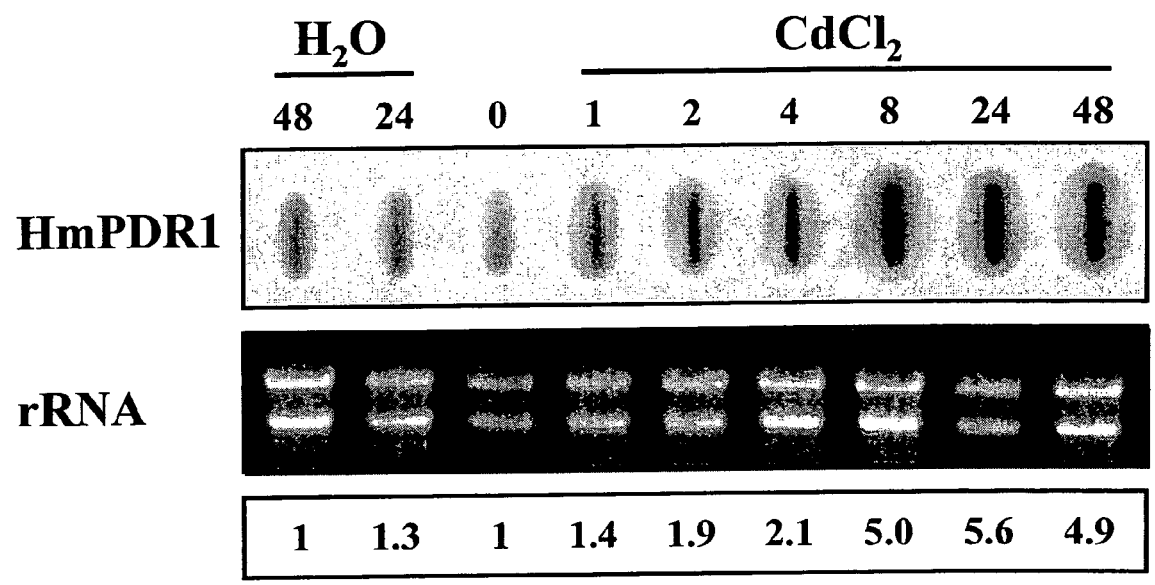
FIG. 3: HmPDR1 expression is induced by $CdCl_2$. Quantitative RT-PCR analysis of HmPDR1 in total RNA from *H. muticus* hairy roots treated with 1 mM $CdCl_2$ or $H_2O$ as a control. Ethidium bromide-stained rRNA is used as a control. The fold increase in the ratio of HmPDR1 transcript to rRNA fluorescence, relative to the value at time point zero, is given below the panels. Time after elicitation is indicated in hours.

To confirm the postulated relationship between the expression of ABC transporter genes and the $CdCl_2$ induced release of alkaloids we performed an expression analysis of the HmPDR1 gene in $CdCl_2$ treated *Hyoscyamus* hairy roots (FIG. 3). Quantitative RT-PCR clearly showed that HmPDR1 is upregulated by $CdCl_2$ elicitation.

5.3 Effect of Heterologous AtPDR1 Expression in Yeast Cells on Alkaloid Tolerance The AtPDR1 gene was subcloned in a yeast expression vector (YCp50) between the 5' and 3' regulatory sequences of the yeast PDR5 gene. This plasmid was then introduced in the yeast AD3 strain (the pdr5 mutant, see Example 1). To analyze the substrate specificity of this plant PDR gene we controlled growth performance of the transformed yeast strains on YPD plates containing the different TAs and NAs as described in example 1. We have shown that the PDR1 gene of *A. thaliana* was able to restore the growth of the pdr5 mutant strain on hyoscyamine and nicotine 5.4 Effect of Heterologous AtPDR1 Expression in BY-2 Suspension Cultured Cells on Alkaloid Tolerance The AtPDR1 gene was transferred to the binary vector pK7WGD2 as described in Example 3.1. BY-2 suspension cultured cells were transformed as described in example 3.2. Control of expression of AtPDR1 is performed by northern blot analysis using a specific DNA probe. To assess tolerance to nicotine and hyoscyamine in transgenic cell lines the same assays as described in Example 3.3 were performed in order to evaluate the functionality of AtPDR1p. Transgenic BY-2 cells showed enhanced tolerance to alkaloids as compared to the control GUS expressing line. However, not to the extent of the ScPDR5-W303 expressing line but comparable to the tolerance levels obtained in the ScPDR5-US50 line.

5.5 Effect of AtPDR1 Expression in BY-2 Suspension Cultured Cells on Nicotinic Alkaloid Production For the analysis of nicotinic alkaloid accumulation, 6-day old recombinant BY-2 cell cultures (pK7WGD2-AtPDR1 en pK7WGD2-GUS) are washed and diluted ten-fold with fresh hormone free MSST medium. After a recuperation period of 12 hours, the cells are treated with methyl jasmonate (MeJA). MeJA is dissolved in dimethyl sulfoxide (DMSO) and added to the culture medium at a final concentration of 50 μM. As a control, cells treated with an equivalent amount of DMSO are included. For alkaloid analysis, the same process is followed as in Example 3.4.

What is claimed is:

1. A method of inducing or enhancing production of at least one secondary metabolite by plant cells, said method comprising:
    transforming plant cells with an expression vector comprising an expression cassette comprising a gene encoding an ABC-transporter;
    wherein said ABC-transporter comprises a Walker A box, a Walker B box, and a Nucleotide Binding Fold;
    wherein said ABC-transporter functions to transport at least one secondary metabolite in plant cells;
    selecting transformed plant cells having an induced or enhanced production of at least one secondary metabolite; and
    propagating such selected transformed plant cells; and
    wherein said gene encoding an ABC transporter comprises a polynucleotide sequence having at least 91% identity to the polynucleotide sequence of SEQ ID NO:1.

2. The method according to claim 1 wherein the secondary metabolites are alkaloids.

3. The method according to claim 1 wherein the ABC-transporters are of plant, fungal, or mammalian origin.

4. The method according to claim 1 wherein the induction or enhancement of the production of at least one secondary metabolite by plant cells results from enhancing the transport of said secondary metabolite into a vacuole.

5. The method according to claim 4 wherein the secondary metabolites are alkaloids.

6. The method according to claim 4 wherein the ABC-transporters are of plant, fungal, or mammalian origin.

7. A method of stimulating the production of secondary metabolites by plants, the method comprising:
    transforming said plants with an expression vector comprising an expression cassette comprising a gene encoding an ABC-transporter;
    wherein said ABC-transporter comprises a Walker A box, a Walker B box, and a Nucleotide Binding Fold; and
    wherein said ABC-transporter functions to transport at least one secondary metabolite in plant cells;
    selecting transformed plants based upon enhanced production of secondary metabolites; and
    propagating such selected transformed plants; and
    wherein said gene encoding an ABC transporter comprises a polynucleotide sequence having at least 91% identity to the polynucleotide sequence of SEQ ID NO:1.

8. The method according to claim 7 wherein the secondary metabolites are alkaloids.

9. The method according to claim 7 wherein the ABC-transporters are of plant, fungal, or mammalian origin.

10. A transgenic plant cell culture displaying an enhanced production of at least one secondary metabolite, wherein said transgenic plant cell is transformed with an expression vector comprising an expression cassette comprising a gene encoding an ABC-transporter;
wherein said ABC-transporter comprises a Walker A box, a Walker B box, and a Nucleotide Binding Fold; and
wherein said ABC-transporter functions to transport at least one secondary metabolite in plant cells; and
wherein said gene encoding an ABC transporter comprises a polynucleotide sequence having at least 91% identity to the polynucleotide sequence of SEQ ID NO:1.

11. The transgenic plant cell culture of claim 10 further characterized in having
(1) an increased vacuolar localization of said at least one secondary metabolite, or
(2) a secretion or an increased secretion of said at least one secondary metabolite.

12. A transgenic plant material selected from the group consisting of a plant, plant cells, plant seeds and plant progeny, said transgenic plant material capable of an enhanced production of at least one secondary metabolite, said transgenic plant material transformed with an expression vector comprising an expression cassette comprising a gene encoding an ABC-transporter;
wherein said ABC-transporter comprises a Walker A box, a Walker B box, and a Nucleotide Binding Fold; and
wherein said ABC-transporter functions to transport at least one secondary metabolite in plant cells; and
wherein said gene encoding an ABC transporter comprises a polynucleotide sequence having at least 91% identity to the polynucleotide sequence of SEQ ID NO:1.

13. The transgenic plant material of claim 12 further characterized in having an increased vacuolar localization of said at least one secondary metabolite.

14. An isolated polynucleotide sequence comprising a sequence having at least 91% identity to the polynucleotide sequence of SEQ ID NO:1;
wherein the isolated polynucleotide sequence induces or enhances production of at least one secondary metabolite in plants.

15. A process for producing a plant cell exhibiting an enhanced production of at least one secondary metabolite, said process comprising:
transforming a plant cell with an expression cassette comprising a gene encoding an ABC-transporter;
wherein said ABC-transporter comprises a Walker A box, a Walker B box, and a Nucleotide Binding Fold;
wherein said ABC-transporter functions to transport at least one secondary metabolite in plant cells; and
selecting transformed plant cells exhibiting enhanced transport of said at least one secondary metabolite into a vacuole; and
wherein said gene encoding an ABC transporter comprises a polynucleotide sequence having at least 91% identity to the polynucleotide sequence of SEQ ID NO:1.

16. A plant cell produced by the process of claim 15.

17. A transgenic plant including the plant cell of claim 16.

18. An isolated polynucleotide useful for producing a plant cell exhibiting an enhanced production of at least one secondary metabolite, said isolated polynucleotide comprising:
a first sequence of nucleotide bases constituting a means for inducing or enhancing production of at least one secondary metabolite in plants or plant cells, and
a second sequence of nucleotides bases, operatively positioned with respect to said first sequence, constituting a means for promoting expression of said first sequence; and
wherein said isolated polynucleotide comprises a polynucleotide sequence having at least 91% identity to the polynucleotide sequence of SEQ ID NO:1.

19. The isolated polynucleotide sequence of claim 14, wherein the isolated polynucleotide sequence comprises the polynucleotide sequence of SEQ ID NO:1.

20. The isolated polynucleotide sequence of claim 14, wherein the isolated polynucleotide sequence encodes the polypeptide sequence of SEQ ID NO:2.

21. A method of inducing or enhancing production or cellular secretion of at least one endogenous secondary metabolite by a plant cell, the method comprising:
transforming the plant cell with an expression vector comprising an expression cassette comprising a gene encoding an ABC-transporter, wherein said ABC-transporter comprises a Walker A box, a Walker B box, and a Nucleotide Binding Fold, and functions to transport at least one secondary metabolite in plant cells;
wherein the secondary metabolite is an endogenous metabolic product of the plant cell, and is transported from the cell to the extracellular space;
wherein the amount of secondary metabolite recoverable from the cell is increased;
selecting a transformed plant cell having an induced or enhanced production of at least one secondary metabolite; and
propagating such selected transformed plant cell; and
wherein said gene encoding an ABC transporter comprises a polynucleotide sequence having at least 91% identity to the polynucleotide sequence of SEQ ID NO:1.

22. The method according to claim 21 wherein the secondary metabolite is an alkaloid.

23. The method according to claim 21 wherein the ABC-transporter is of plant, fungal, or mammalian origin.

* * * * *

UNITED STATES PATENT AND TRADEMARK OFFICE
CERTIFICATE OF CORRECTION

| | | |
|---|---|---|
| PATENT NO. | : 7,622,634 B2 | |
| APPLICATION NO. | : 10/666778 | |
| DATED | : November 24, 2009 | |
| INVENTOR(S) | : Alain Goossens et al. | |

It is certified that error appears in the above-identified patent and that said Letters Patent is hereby corrected as shown below:

| | | |
|---|---|---|
| COLUMN 15, | LINE 65, | change "systems fur" to --systems for-- |
| COLUMN 17, | LINE 17, | change "carbenicilin" to --carbenicillin-- |
| COLUMN 17, | LINE 22, | change "carbenicilin" to --carbenicillin-- |
| COLUMN 20, | LINE 55, | change "nicotine" to --nicotine.-- |
| COLUMN 21, | LINE 6, | change the word at the end of the line "en" to --in-- |

CLAIM 18, COLUMN 58, LINE 15,   change "nucleotides bases," to --nucleotide bases,--

Signed and Sealed this
Twenty-seventh Day of September, 2011

David J. Kappos
*Director of the United States Patent and Trademark Office*